(12) United States Patent
Naidu et al.

(10) Patent No.: US 8,309,080 B2
(45) Date of Patent: Nov. 13, 2012

(54) METALLO-PROTEIN AND TOCOTRIENOL (MP-T3) COMPOSITIONS AND USES THEREOF

(75) Inventors: A. Satyanarayan Naidu, Santa Ana, CA (US); A. G. Sreus Naidu, Santa Ana, CA (US); A. G. Tezus Naidu, Santa Ana, CA (US)

(73) Assignee: Naidu LP, Pomona, CA (US)

( * ) Notice: Subject to any disclaimer, the term of this patent is extended or adjusted under 35 U.S.C. 154(b) by 662 days.

(21) Appl. No.: 12/327,712

(22) Filed: Dec. 3, 2008

(65) Prior Publication Data

US 2009/0148433 A1 Jun. 11, 2009

Related U.S. Application Data

(60) Provisional application No. 61/012,008, filed on Dec. 6, 2007.

(51) Int. Cl.
*A61K 38/47* (2006.01)

(52) U.S. Cl. ............... 424/94.61; 424/655; 424/682; 424/687; 424/702; 514/1.1; 514/2.5; 514/13.3

(58) Field of Classification Search .............. None
See application file for complete search history.

(56) References Cited

U.S. PATENT DOCUMENTS

| | | | |
|---|---|---|---|
| 6,172,040 B1 | 1/2001 | Naidu | |
| 7,074,759 B2 | 7/2006 | Naidu | |
| 7,125,963 B2 | 10/2006 | Naidu | |
| 7,601,689 B2 | 10/2009 | Naidu | |
| 7,956,031 B2 | 6/2011 | Naidu et al. | |
| 8,003,603 B2 | 8/2011 | Naidu | |
| 2002/0123460 A1* | 9/2002 | Kung et al. | 514/8 |
| 2005/0095301 A1* | 5/2005 | Deshpande | 424/490 |
| 2007/0253941 A1* | 11/2007 | Naidu et al. | 424/94.1 |
| 2008/0254018 A1 | 10/2008 | Naidu | |
| 2011/0200575 A1 | 8/2011 | Naidu et al. | |
| 2011/0286986 A1 | 11/2011 | Naidu et al. | |
| 2011/0286989 A1 | 11/2011 | Naidu | |

OTHER PUBLICATIONS

Qureshi et al., Am J Clin Nutr., 1991, vol. 53, p. 1021S-1026S.*
Takeuchi et al., British Journal of Nutrition, 2004, vol. 91, p. 533-538.*
Qureshi et al., J Nutr., 2001, vol. 131, p. 223-230.*
Onning et al., Ann Nutr Metab., 1999, vol. 43, Abstract.*
Gallaher et al., J Nutr, 2000, vol. 130, p. 2753-2759.*
Soncin et al., Biochemical and Biophysical Research Communications, 1997, vol. 236, p. 604-610.*

* cited by examiner

*Primary Examiner* — Kade Ariani
(74) *Attorney, Agent, or Firm* — Knobbe, Martens, Olson & Bear, LLP (57) ABSTRACT

Metallo-proteins including but not limited to lactoferrin (LF), transferrin (TF) and ovotransferrin (OTF) (all members of transferrin family), ceruloplasmin (CP) and metallo-thionein (MT) were found to stabilize and enhance the bio-functional activity of tocotrienol (T3), T3 mixtures or derivates. The synergism between MP and T3 also promote the intestinal transfer and the ultimate bio-availability of T3 and T3-derivatives for physiological functions. Such functional synergism includes hypocholesterolemic, anti-thrombotic, antioxidant, anti-athermogenic, anti-inflammatory and immuno-regulatory activities of T3 agents. These T3 compositions are useful as pharmaceuticals, in cosmetics, in foods and as nutritional supplements.

24 Claims, 1 Drawing Sheet

METALLO-PROTEIN AND TOCOTRIENOL (MP-T3) COMPOSITIONS AND USES THEREOF

RELATED APPLICATIONS

This application claims priority to provisional U.S. Application No. 61/012,008, filed Dec. 6, 2007 which is incorporated herein by reference.

BACKGROUND OF THE INVENTION

1. Field of the Invention

Embodiments of the invention relate to stabilized compositions containing tocotrienols. In particular, compositions are stabilized by use of a metallo-protein such as lactoferrin, transferrin, ovotransferrin, ceruloplasmin, metallo-thionein and metallo-protein complexes. The compositions are useful to treat conditions such as hyperlipidemia, hypercholesteremia, atherosclerosis, diabetes and neurodegenerative diseases.

2. Description of the Related Art

Vitamin E is one of the most important phytonutrients in edible oils. There are eight naturally occurring vitamers (substances having similar vitamin activity) of vitamin E. They consist of tocopherols and tocotrienols, structurally similar molecules containing a two-ringed 'chromanol head' and a 16-carbon 'phytyl tail'. In the tocopherols, the phytyl tail is saturated; in the tocotrienols it contains three double (unsaturated) bonds. All natural E vitamers are in a spatial form known as the R,R,R-stereoisomer conformation. (Theriault A, et al. Clin Biochem 32:309-319, 1999)

Tocotrienols (T3) are found primarily in the oil fraction of rice bran, palm fruit, barley, and wheat germ. Natural T3 exists in four different forms or isomers, named alpha-(5,7, 8-trimethyl), beta-(5,8-dimethyl), gamma-(7,8-dimethyl) and delta-(8-monomethyl), which contain different number of methyl groups on the chromanol ring. Although all the isomers are potent free radical scavengers due to the ease of donating a hydrogen atom from the hydroxyl group on the chromanol ring, each T3 form exhibits a distinct biological activity. (Tan B. J Am Nutr Assoc 8:35-42, 2005)

T3 concentrates and isomers can be obtained through purification processes from several natural sources such as palm olein and rice bran oil. These T3 isolation procedures are intricate and difficult to do on a large scale. The Malaysian Palm Oil Board (MPOB) spearheaded extensive research and development in oil palm cultivation and revolutionized the global production of palm oil T3 and T3 derivatives for food and pharmaceutical applications.

U.S. Pat. No. 6,838,104 teaches a process to recover high yields of T3 compounds from biological sources such as palm oil, cereals, grains, and grain oils. U.S. Pat. No. 6,395,915 describes a large-scale process to isolate T3 isomers from tocopherols using reverse phase partition liquid chromatography. U.S. Pat. No. 6,224,717 describes a method for separating T3 from tocol admixtures. U.S. Pat. No. 5,670,668 discloses isolation and purification of D-gamma-T3 by crystallization and recrystallization procedures.

Several synthetic methods to derive d-T3 compounds from various organic chemicals are known in the prior art. U.S. Pat. No. 7,038,067 describes a method to synthesize D-T3 from a (2S)-vinyl-chromane compound, through hydroboration of the (2S)-vinyl-chromane to provide an organoborane, followed by coupling the organoborane with a halogenated C-14 side-chain compound under conditions of palladium-catalyzed cross-coupling. US Patent Application 20050124687 discloses a process to derive d-T3 from a (2S) 2-hydroxymethyl-6-hydroxy-alkylchroman compound, through reaction with a famesyl Grignard or sulfone compound.

Functional Properties of T3 Compounds

T3s have been attributed with several nutritional and health benefits. The primary function of T3 is to serve as an antioxidant. Epidemiological studies demonstrate a positive relationship between T3 and the prevention of atherosclerosis and vascular diseases, even those affecting the brain. T3 can promote the breakdown of homocysteine by lessening the adverse impact of oxidants on endothelial function and enhance gastric healing. The protective effect of T3 against viral or bacterial infections in experimentally challenged young animals has been reported. Resistance to the flu was demonstrated in both young and old test animals. T3 supplementation may help to prevent age-related macular degeneration. T3s are also needed for the health of cellular membranes, which may help prevent blood clotting, protect lungs against toxic damage, and can help with boosting immune function. T3s have been reported to have activity as anti-tumor agents and neuro-protective agents (Schaffer S, et al. *J Nutr* 35:151-154, 2005). The major functional activities of T3 are elucidated below.

Management of serum cholesterol: A high blood cholesterol level is one of the major risk factors for cardiovascular diseases. T3 has a number of beneficial properties in cholesterol reduction and reversing atherosclerosis. The interaction of T3 with the mevalonate pathway leads to the lowering of serum cholesterol levels. Several studies revealed that supplementation with T3 or T3-rich fractions (TRF) results in significant reduction in serum total cholesterol (15-42%) and low-density lipoprotein (LDL) cholesterols (8-62%) in chicken and hyperlipidemic pigs. (Qureshi A A, et al. *Am J Clin Nutr* 53:1021-1026, 1991; Qureshi A A, et al. *Lipids* 30:1171-1177, 1995; Black T M, et al. *J Nutr* 130:2320-2426, 2000; Chao J T, et al. *J Nutr Sci Vitaminol* 48:332-337, 2002).

Different T3 isomers show varying degrees (about 30-fold) of cholesterol-lowering ability. Accordingly, T3 isomers inhibit cholesterol synthesis, in decreasing order, delta-T3>gamma-T3>alpha-T3>beta-T3. Concurrent administration of alpha-tocopherol seems to interfere with the hypocholesterolemic effects of T3. Thus, limiting tocopherols within 20% of tocols mixture is proposed to achieve better therapeutic activity. The counter action among vitamin E analogs was more obvious when serving T3 at a high dose due to more conversion of T3 to tocopherol in the plasma. (Qureshi A A, et al. *Am J Clin Nutr* 53:1021-1026, 1991; Qureshi A A, et al. *J Nutr* 126:389-394, 1996; Qureshi A A et al., *J Agric Food Chem* 48:3130-3140, 2000).

The molecular mechanism for suppression of cholesterol biosynthesis by T3 has been ascribed to the side-chain's unique ability to increase cellular famesol, a mevalonate-derived product, which signals the proteolytic degradation of 3-hydroxy-3-methylglutaryl-coenzyme (HMG-CoA) reductase activity. This mechanism differs from that of 'statins', the well-known HMG-CoA inhibitors, which block the enzyme as a chemical analog of substrate HMG-CoA, by competitive inhibition. (Qureshi A A, et al. *J Biol Chem* 261:10544-10550, 1986; Parker R A, et al. *J Biol Chem* 268:11230-11238; Correll C C, Edwards P A. *J Biol Chem* 269:633-638, 1994).

Management of serum cholesterol levels could reduce the risk of cardiovascular disease, one of the most important causes of morbidity and mortality, especially in men and women >60 years old. Most popular and effective anti-cholesterol drug is 'statin' (Atovastatin, Simvastatin, Lovastatin, Pravastatin, etc.) which occupy $22 billion annual market for hypercholesterolemia patients. Since statins suppress serum cholesterol by competing with liver HMG-CoA, they also inhibit the production of intermediary substances within the mevalonate chain. One affected product is 'Coenzyme-Q10' which is essential for healthy heart function and proper nerve conduction. Other side effects involve rhabdomyolysis and peripheral neuropathy.

Such adverse effects were not reported with T3 administration, based on controlled clinical trials with hypercholesterolemia patients. Yet another benefit of T3 application is that it reduces total cholesterol and LDL cholesterol (bad cholesterol), while slightly increases the concentration of HDL (good cholesterol) in some cases.

Anti-tumor effects: Due to significant differences in the chemical structure, the anti-tumor activity of T3 is more potent than the common forms of tocopherol. Unsaturated side-chain in the T3 structure makes this molecule more efficient in penetrating tissues that are made of saturated fatty layers. Several studies demonstrated that T3s have an anti-proliferative effect on human, mouse and rat tumor cells.

A T3-rich fraction (TRF) from palm oil inhibits the growth of human breast cancer cells in a dose-dependent manner, increasing apoptosis (programmed cell death) through modulation of several genes. When human breast cancer cells were injected into athymic (immune deficient) mice, feeding 1 mg/day of a palm oil TRF for 20 weeks delayed the onset of tumor growth and reduced their number and size. The tumors of the treated animals showed different patterns of gene activation and suppression compared to those of untreated animals. (Nesaretnam K, et al. *Lipids* 33:461-469, 1998; Nesaretnam K, et al. *Lipids* 39:459-67, 2004).

The T3 mediated growth inhibition of human breast cancer cells in vitro as well as in vivo seems to be through estrogen-independent mechanisms. T3s can also affect cell homeostasis, possibly independently of their antioxidant activity. Anti-cancer effects of alpha-T3 and gamma-T3 have been reported, although delta-T3 was verified to be the most effective tocotrienol in inducing apoptosis (cell death) in estrogen-responsive and estrogen-nonresponsive human breast cancer cells. A daily dose of 30-50 mg mixture of alpha- and gamma-tocotrienols can reduce breast cancer risk, and a treatment plan for breast cancer should use higher dosage. (Nesaretnam K, et al. *Ann NY Acad Sci* 1031:143-157, 2004).

Investigation of the anti-proliferative effect of T3 against prostate cancer cells suggests that the activity of vitamin E is mostly a detoxification mechanism. (Conte C, et al. *Ann NY Acad Sci* 1031:391-394, 2004).

Neuro-protective effects: Oxidative stress is a factor in the development of some neurodegenerative diseases. Cell culture studies have shown that T3 protects neurons from oxidative stress-induced apoptosis. The T3's, particularly alpha-T3, have been reported to have much greater activity in neuron protection than the tocopherols (Khanna S, et al. *J Biol Chem* 278:43508-43515, 2003; Sen C K, et al. *Ann NY Acad Sci* 1031:127-42, 2004; Osakada F, et al. *Neuropharmacology* 47:904-915, 2004)

Oral supplementation of palm oil T3 complex to spontaneously hypertensive rats led to increased T3 level in the brain. The rats supplemented with T3 showed more protection against stroke-induced injury compared to controls (non-supplemented group). This study demonstrated that oral supplementation of the palm T3 complex acts on key molecular checkpoints (C-Src and 12-lipoxygenase) to protect against glutamate- and stroke-induced neuro-degeneration and ultimately may protect against stroke in vivo. (Khanna S, et al. *Stroke* 36:2258-2264, 2005).

Diabetes management: Investigation of the intake of antioxidants for their ability to prevent type 2 diabetes shows that vitamin E intake was significantly associated with a reduced risk of type 2 diabetes. The relative risk (RR) of type 2 diabetes between the extreme quartiles of the intake was 0.69 (95% CI 0.51-0.94, P for trend=0.003). Intakes of alpha-tocopherol, gamma-tocopherol, delta-tocopherol, and beta-T3 were inversely related to a risk of type 2 diabetes. Thus the development of type 2 diabetes may be reduced by the intake of antioxidants in the diet. (Montonen J, et al. *Diabetes Care* 27:362-366, 2004).

U.S. Pat. Nos. 4,603,142; 6,262,109; 6,557,064; and 6,977,270 are related to the benefits of administering T3 and T3-derivates as antioxidants and nitrogen oxide scavengers to treat and prevent various health conditions and compositions of T3 and T3-derived compounds to lower serum levels of cholesterol.

Furthermore, T3 and T3-derived compositions for treating and/or ameliorating the symptoms of inflammation (U.S. Pat. No. 7,081,476); cerebral ischemia (U.S. Pat. No. 7,034,054); type 2 diabetes mellitus (U.S. Pat. No. 7,060,295); tumors (U.S. Pat. No. 6,441,029) have also been described.

Limitations of T3 Use for Health Applications

Though endowed with a myriad of prophylactic and therapeutic benefits, the functionality of T3 compounds depend on their physico-chemical stability. Milieu factors such as pH, temperature, aeration (oxygen), humidity, ultraviolet light and co-existent chemical compounds such as halogens (eg. Fluorides, Chlorides), alkalis, trace metals (especially iron, copper and zinc), either individually or collectively could affect the stability and functionality of T3 compounds.

All types of vitamin-E (T3 and tocopherol) isomers are highly sensitive to temperature and oxygen. Each isomer exhibits different sensitivity to high temperature and among tested isomers, alpha-T3 degrades more rapidly and severely than others. Under 0% oxygen conditions, no degradation could be observed even when T3 isomers are exposed to 95° C. for 4 h. However, as low as 2% oxygen results in the degradation of gamma-tocopherol and gamma-T3 by 20% and 29%, respectively.

All forms of vitamin E, the T3 isomers in particular, are relatively unstable and readily degrade upon contact with polyunsaturated or rancid fats and oils. Furthermore, aqueous systems that may contain chlorine or ozone could quickly denature T3 compounds and markedly reduce their intestinal absorption.

The short-time antioxidant activity of T3 agents and their relative instability (short shelf life) in the presence of oxygen at typical environmental temperatures is a major limitation in use of T3 in prophylactic for therapeutic formulations.

Furthermore, the short survival time of T3 agents in the gut milieu and poor diffusion across the intestinal mucosal barrier are crucial setbacks for their health applications. Furthermore, the lack of specific transporter molecules to facilitate and enhance the bioavailability of T3 compounds is a serious shortcoming in the exploitation of these broad-spectrum agents in human and animal health.

The present invention categorically addresses the above limitations of T3 and T3-derivates. It further describes methods to synergistically enhance the functional properties and bio-availability of T3 and T3-derivatives in promoting intestinal absorption.

Metal Antagonists that Inhibit T3 Activity

Antagonists that interfere with the functional activity of T3 and T3-derivatives include metallic compounds such as iron, copper, and zinc. Due to the presence of these metal cations in various foods we consume, this antagonistic effect against T3 compounds is manifested multi-fold in the gastro-intestinal tract, especially when T3 is consumed as a dietary supplement.

Iron

Iron ($Fe^{+3}$): Iron is a remarkably useful metal in Nature, but iron, if not sequestered safely during transport or storage, could become hazardous due to its ability to generate free radicals. Biological examples include Fenton Chemistry leading to the formation of highly reactive species, such as the hydroxyl radical (.OH) and the ferryl ion ($FeO^{2+}$), and lipid peroxidation. Furthermore, accumulation of iron in excess of physiologic requirements has been implicated in risk of cardiovascular disease because of increased iron-catalyzed free radical-mediated oxidative stress. (Zacharski L R et al. *JAMA* 297:603-610, 2007).

The need to conserve body iron stores has closely evolved with an essential requirement for antioxidant protection and, several 'acute-phase' proteins involved in iron metabolism such as haptoglobins and hemopexin in collaboration with the iron-binding proteins transferrin and Lactoferrin (LF) contribute to cellular defense against oxidative damage.

Copper

Copper ($Cu^{+2}$): Copper is involved in the function of several enzymes and is required for infant growth, host defense mechanisms, bone strength, red and white cell maturation, iron transport, cholesterol and glucose metabolism, myocardial contractility, and brain development. Dietary copper was approximately one hundred times more active in lowering cholesterol in plasma than was clofibrate which, in turn was six times as active as dietary fat. Dietary copper may be a powerful determinant of cholesterolemia. (Klevay L M. *Med Hypotheses*. 24:111-119, 1987; Olivares M, Uauy R. *Am J Clin Nutr* 63:791S-796S, 1996).

Zinc

ZINC ($Zn^{+2}$): Lipid peroxidation and LDL oxidation are risk factors for arteriosclerosis, and consequently angina pectoris. Administration of biologically available zinc was a beneficial treatment in a significant percentage of patients with severely symptomatic, inoperable atherosclerotic disease. Although prevention of cholesterol-induced arteriosclerosis by zinc is predicted from findings related to oxidative stress and lipid peroxidation, removal of LDL might be attributable to action of ionic zinc on Intercellular Adhesion molecule (ICAM) inhibition. In stark contrast to current practice, high-dose zinc should be considered as basic in prophylaxis and therapy for atherosclerosis to ameliorate angina pectoris and restore youthful cardiac function. (Eby G A, Halcomb W W. *Med Hypotheses* 66:169-172, 2006).

In vivo and in vitro ability of metallo-proteins (MPs) to chelate bio-metals such as iron, copper, and zinc is well known. However, to exploit this high-affinity metal binding phenomenon to protect T3 and T3 derivatives from such functional antagonists has not been reported.

Figure 1:
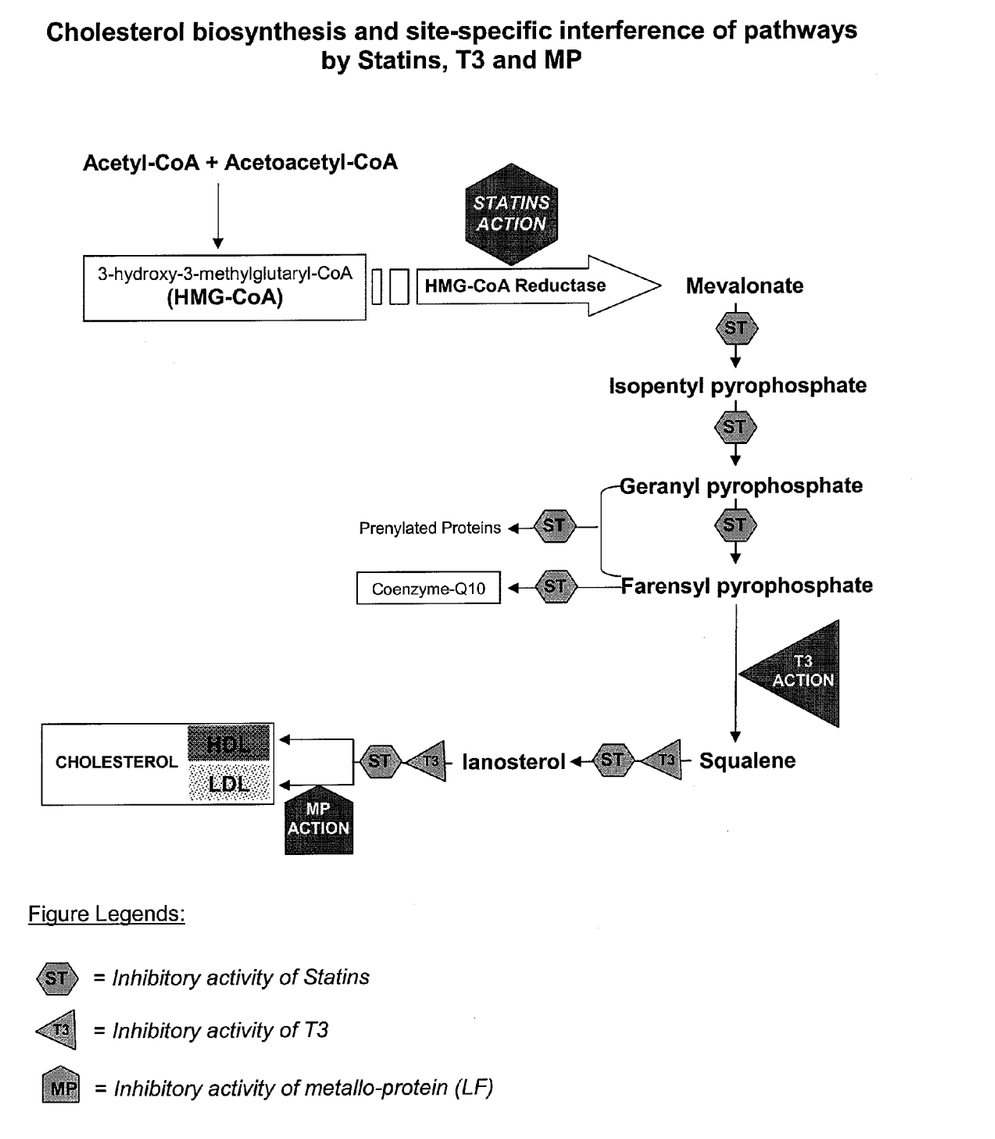
FIG. 1 shows cholesterol biosynthesis and site-specific interference of pathways by statins, tocotrienol (T3) and metallo-protein (MP).

Furthermore, the present inventor has discovered that the combination between MP and T3 compounds not only provided chemical stability, but surprisingly enhanced the functional properties of both molecules in a synergistic manner. Accordingly, the MP-T3 mixture demonstrated (i) increased bio-availability of T3 via intestinal receptors that are specific for MP (i.e. lactoferrin) transport; and ii) regulatory function of MP at specific steps distinct from T3 interference mechanisms in cholesterol biosynthesis, which formed a powerful basis to develop methods to treat various physiological conditions, in particular, hyperlipidemia (FIG. 1).

Metallo-Proteins to Overcome T3 Limitations

Living organisms sequester elements such as iron, copper, zinc, etc from the environment to utilize these compounds in highly critical biological pathways. During evolution, specific metallo-proteins (MP) have emerged for transport of these essential metal ions for specific physiological functions. Most of the MPs also work as regulatory molecules in monitoring the levels of essential metals in the body. Such metallo-regulation is important, as any elevated levels of iron, copper or zinc could lead to cellular toxicity via pro-oxidative mechanisms.

These metal-binding, -transport, -regulation and antioxidant properties make the MPs highly attractive as multi-functional molecules to protect and stabilize compounds that are sensitive to metal-induced oxidative damage—such as T3. However, no such methods have been described in the prior art to utilize MP for molecular protection and structural stabilization of T3 compounds.

Lactoferrin (LF), a multi-functional MP from milk protein has been shown to inhibit oxidation in buffered corn oil emulsions and lecithin liposome systems at pH 6.6 and 50° C. Mixtures of LF and ferrous ions are more potent antioxidants than LF alone. LF demonstrates a pro-oxidant activity in buffered liposomes. Copper was a stronger pro-oxidant than iron in buffered emulsions and LF could decrease the pro-oxidant effect of iron, but not of copper, in emulsions. The antioxidant or pro-oxidant activities of LF depended on the lipid system, buffer, its concentration, the presence of metal ions, and oxidation time. (Huang S W, et al. *J Agric Food Chem* 47:1356-1361, 1999). However, the reference does not suggest the use of LF to protect and stabilize T3 and T3-derivatives.

Lactoferrin

Lactoferrin (LF) is a bi-lobed glycoprotein belonging to the transferrin family of iron-binding MPs. LF is present in milk and various mammalian secretions that bathe the mucosal surfaces. LF has ability to reversibly bind two $Fe^{3+}$ ions per lobe in coordination with two $CO_3^{2-}$ ions. LF can release the bound iron in a fully reversible manner, either on exposure to lowered pH (below 4.0) or on receptor binding. This high affinity for iron is linked to many of its biological functions, including antimicrobial, antioxidant, anti-tumor, immuno-modular, and nutraceutical effects. In addition to ferric ions, LF binds to other metal ions such as copper, zinc, manganese (III), cobalt (III), aluminum (III), and lanthanum (IV) ions.

LF is shown to inhibit accumulation of cellular cholesteryl esters (CE), in a dose-dependent manner. In the presence of bovine milk LF, accumulation of CE in the macrophages incubated with acetylated low-density lipoproteins (LDL) decreased by more than 80%. LF also blocks the binding of acetylated LDL to macrophages. LF binds acetylated or oxidized LDL and neutralizes their negative charges. Furthermore, LF inhibits the binding of modified LDLs to macrophages by direct interaction with modified LDLs, resulting in their loss of function as ligands for the scavenger receptor. Modification of arginine residues with 1,2-cyclohexanedione abolished its ability to bind to acetylated LDL, suggesting that a region rich in basic amino acid residues near the N-terminus of LF, which resembles the ligand-binding site of the scavenger receptor, may be responsible for this binding ability. These results suggest the possibility that LF in the blood stream may act as an anti-atherogenic agent in vivo. (Kajikawa M, et al. *Biochim Biophys Acta* 1213:82-90, 1994).

Furthermore, oral administration of bovine milk LF reduces plasma or hepatic triacylglycerol and cholesterol and increases the high density lipid (HDL)-cholesterol levels. These changes in plasma lipid profiles were accompanied by significant decreases in hepatic cholesterol and triacylglycerol contents. Interestingly, LF also showed a suppressive effect on the lymphatic triacylglycerol absorption in vivo. (Takeuchi T, et al. *Br J Nutr* 91:533-538, 2004).

U.S. Pat. No. 7,026,295 relates to methods of using LF to reduce circulating levels of cholesterol and vascular inflammation, in order to treat, prevent or reduce the incidence of atherosclerosis and cardiovascular disease.

The use of LF to stabilize T3 and T3-derivatives, and as a functional synergist in MP-T3 mixtures for clinical management, which includes but is not limited to hyperlipidemia, atherosclerosis and other cardiovascular diseases, has not been previously described.

Ceruloplasmin

Ceruloplasmin (CP) is an important plasma blue-copper protein (alpha-2-globulin) with a multifunctional role. As an oxidase enzyme (EC 1.16.3.1), CP is involved in the regulation of the level of biogenic amines and phenols. Also known as Ferroxidase I, CP catalyses the $Fe^{2+}$ to $Fe^{3+}$ reaction (an important reaction considering that $Fe^{2+}$ catalyze the Fenton reaction which produces the highly toxic hydroxy radical from $H_2O_2$). CP is also an important oxygen free radical (OFR) scavenger. Recently, CP was shown to be involved in angiogenesis, in relation with its function as copper carrier. (Gutteridge and Stocks, 1981).

CP is believed to play a critical role in oxidizing copper and participates in the acute phase reaction to stress. An antioxidant activity for CP has been described, but recent evidence suggests that the protein may also exhibit potent pro-oxidant activity and cause oxidative modification of low density lipoprotein (LDL). The pro-oxidant activity is highly dependent on the structure of the protein; removal of a single one of the seven integral copper atoms, or a specific proteolytic cleavage event, completely suppresses LDL oxidation. (Fox P L, et al. *Life Sci* 56:1749-1758, 1995).

The use of CP to stabilize T3 and T3-derivatives, and as a functional synergist in MP-T3 mixtures for clinical management, which includes but is not limited to hyperlipidemia, atherosclerosis and other cardiovascular diseases, has not been previously described.

Metallo-Theonine

Metallo-theonine (MT) belongs to the group of intracellular, cysteine-rich proteins with molecular weight from 6 to 10 kDa. MTs have a high affinity for essential, as well as toxic, trace metals. MTs are widely distributed throughout living organisms and are fairly well conserved in humans, mammals, plants, and fungi. Different isoforms of MT exist in the human body. MT1 and MT2 are generally found in the liver and kidney. A third isoform, MT0, is also known to exist in human fetal liver (HFL). Other isoforms such as MT3 and MT4 are reported to be expressed in the brain and in mouse tissues containing stratified squamous epithelial cells, respectively. (Ecker D J, et al. *J Biol Chem* 261:16895-16900, 1986; Kaegi J H R, Kojima Y. *Experientia* 52:25-62, 1987).

MTs are intracellular proteins, characterized by their unusual high cysteine content (30%) and lack of aromatic amino acids. Because of their rich thiol content, MTs bind a number of trace metals including cadmium, mercury, platinum and silver, and also protect cells and tissues against heavy metal toxicity. Additionally MTs are among the most abundant intracellular aspects for biologically essential metals, zinc and copper. MT metal-thiolate fractions being dynamic and of high affinity also facilitate metal exchange in tissues. They are present in a great variety of eukaryotes, functioning as anti-oxidants; they also play a protective role against hydroxyl free radicals. (Thirumoorthy N, et al. *World J Gastroenterol* 13:993-996, 2007; Hamer D. *Annu Rev Biochem* 55:913-952, 1986).

Metallo-thionein (MT), the zinc-binding protein regulates Zn (II) metabolism in the body. This protein also binds with high affinity to other heavy metals such as cadmium, Cd (II); mercury, Hg (II); platinum, (Pt); and silver, Ag (II) to protect the body from heavy metal toxicity. MT is present in a variety of eukaryotes and functions as a potent antioxidant, with a protective role against hydroxyl free radicals (Thirumoorthy N, et al. *World J Gastroenterol* 13:993-996, 2007)

The use of MT to stabilize T3 and T3-derivatives, and to use MT as a functional synergist in MP-T3 mixtures for clinical management, which includes but is not limited to hyperlipidemia, atherosclerosis and other cardiovascular diseases, has not been previously described.

SUMMARY OF THE INVENTION

Embodiments of the invention are directed to compositions which include tocotrienol (T3) and at least one metalloprotein. Preferably, the T3 is from a natural source. More preferably, the T3 is a mixture of tocotrienols that may include two or more of alpha-T3, beta-T3, gamma-T3 and delta-T3 forms or isomers.

In preferred embodiments, the natural source is oil or an oleoresin powder such as wheat germ, barley, saw palmetto, palm and rice bran. More preferably, the natural source is palm oil, palm oleoresin powder, rice bran oil or rice bran oleoresin powder.

In preferred embodiments, the metallo-protein is transferrin, ovotransferrin, ceruloplasmin, metallo-thionein, lactoferrin and combinations thereof. In a most preferred embodiment, the metallo-protein is a combination of lactoferrin and angiogenin.

In a preferred embodiment, the composition includes at least one angiogenic factor selected from the group including but not limited to vascular endothelial growth factors (VEGF), fibroblast growth factors (FGF), transforming growth factors (TGF) and angiogenin.

In preferred embodiments, the composition includes one or more of the following: coenzyme Q10, nattokinase, one or more vitamins, one or more phytophenolic compounds, one or more phytosterols, and/or one mineral supplement.

In preferred embodiments, the at least one vitamin is selected from Vitamin A, Vitamin C, Vitamin E (alpha, beta, gamma and delta forms of tocopherols), Vitamin D, and Vitamin K and B vitamins including thiamine (Vitamin B1), Riboflavin (Vitamin B2), Niacin/Vitamin B3 (defined as nicotinic acid, nicotinamide, NAD, NADH and NADP), Pantothenic acid (Vitamin B5), Pyridoxine and Pyridoxamine (Vitamin B6), Biotin (Vitamin B7), Folic Acid (Vitamin B9) and Cobalamin (Vitamin B12).

In preferred embodiments, the at least one phytophenolic compound is selected from polyphenols, flavonoids and flavonoid glycosides such as oligomeric procyanidins, anthocyanidins, tannins, flavan-3-ols, flavonols, flavanones, isoflavones, flavones, fisetin, 5,7,3',4',5'-pentahydroxyflavone, luteolin, 3,6,3',4'-tetrahydroxyflavone, quercetin, 7,3',4',5'-tetrahydroxyflavone, kaempferol, 6-hydroxyapigenin, apigenin, 3,6,2',4'-tetrahydroxyflavone, 7,4'-dihydroxyflavone, 7,8,3',4'-tetrahydroxyflavone, 3,6,2',3'-tetrahydroxyflavone, 4'-hydroxyflavone, 5,4'-dihydroxyflavone, 5,7-dihydroxyflavone, morin, flavone, 5-hydroxyflavone, daidzein, 3,5,7,3',4'-pentahydroxy flavanone, epicatechin, catechin, gallocatechin, epigallocatechin, epigallocatechin gallate, gallocatechin gallate, epicatechin gallate, catechin gallate, myricetin, isorhamnetin, pachypodol, rhamnazin, luteolin, tangeritin, hesperetin, naringenin, eriodictyol, dihydroquercetin, dihydrokaempferol, laricitrin, syringetin, quercitrin, myricitrin, rutin, vitexin, daidzin, gallic acid, ellagic acid, p-hydroxybenzoic acid, protocatechuic acid, genistin, cosmosiin, apiin, orientin, glycitein, cyanidin, delphinidin, malvidin, pelargonidin, peonidin, petunidin, caffeic acid, cinnamic acid, coumaric acid, ferulic acid, isoferulic acid, curcumin, chlorogenic acid, rosmarinic acid and verbscoside.

In preferred embodiments, the at least one phytosterol is selected from campesterol, beta-sitosterol, and stigmasterol.

In preferred embodiments, the at least one mineral supplement is selected from calcium, magnesium, chromium, and selenium in appropriate form, such as a pharmaceutically acceptable salt.

Embodiments of the invention are also directed to food or drink compositions which include any of the compositions described above.

Embodiments of the invention are directed to lowering levels of LDL cholesterol by administering a composition which includes tocotrienol (T3) and at least one metalloprotein to an individual in need thereof at a dosage sufficient to lower LDL cholesterol. Preferably, the T3 is from a natural source.

In preferred embodiments, the cholesterol-lowering composition additionally includes at least one additional component which is an amino acid such as arginine, citrulline, carnitine, methionine or lysine.

In preferred embodiments, the cholesterol-lowering composition additionally includes a cholesterol lowering drug. In preferred embodiments, the cholesterol lowering drug is cholestyramine, colestipol, clofibrate, colesevelam (WelChol), gemfibrozil, fenofibrate (Tricor), Ezetimibe (Zetia), Lovastatin (Mevacor), Simvastatin (Zocor), Pravastatin (Pravachol), Fluvastatin (Lescol), Rosuvastatin Calcium (Crestor), Atorvastatin (Lipitor) or combinations thereof.

In preferred embodiments, the administered dosage is about 10-1000 mg of T3 per day, more preferably about 25-250 mg of T3 per day.

Embodiments of the invention are directed to methods of treating a disease condition by administering a composition which includes tocotrienol (T3) and at least one metalloprotein (MP) to an individual in need thereof. Preferably, the MP-T3 mixture is from a natural source. Preferably, the disease condition is diabetes, neurodegenerative diseases, cardiovascular diseases, atherosclerosis or hypercholesterolemia.

Embodiments of the invention are directed to kits having a first composition which includes tocotrienol (T3), preferably from a natural source, and at least one metalloprotein; and a second composition which includes a soluble fiber. Preferably, the T3 is a mixture of tocotrienols that includes alpha-T3, beta-T3, gamma-T3 and delta-T3 forms or isomers. Preferably, the natural source is palm oil in beadlet form.

In preferred embodiments, the metallo-protein includes lactoferrin and angiogenin.

In preferred embodiments, the first composition also includes Vitamin $B_3$ as nicotinamide, calcium-D-pantothenate (Vitamin $B_5$), and Biotin (Vitamin $B_7$).

In preferred embodiments, the first component is in tablet or capsule form and the second component is administered as a liquid. More preferably, the second component is a dry powder or concentrate that is mixed with a liquid before administration.

In preferred embodiments, the soluble fiber in the second composition is glucomannan, maltodextrin, or a combination.

Preferably, the first composition also includes calcium (as carbonate), magnesium (as stearate or oxide), chromium (as nicotinate), and selenium (as 1-selenomethionine).

Embodiments of the invention are directed to methods of treating hypercholesterolemia, hyperlipidemia and/or hyperlipoproteinemia by administering to an individual in need thereof in any order: a first composition which includes T3 and a metalloprotein; and a second composition which includes a soluble fiber at a dosage sufficient to treat hypercholesterolemia, hyperlipidemia or hyperlipoproteinemia. Preferably, the T3 is from a natural source. Preferably, the first composition is in tablet or capsule form and the second component is administered as a liquid. In preferred embodiments, the administered dosage is 10-1000 mg of T3 per day, more preferably, 25-250 mg of T3 per day.

Further aspects, features and advantages of this invention will become apparent from the detailed description of the preferred embodiments which follow.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

It has now been surprisingly found that T3 and T3-like compounds stabilized with metallo-proteins (MPs) such as LF, ovotransferrin (OTF), CP, MT and their derivatives reduce serum total cholesterol, LDL cholesterol, apo-lipoprotein B and triglyceride levels in mammals. Embodiments of the invention provide methods for reducing mammalian serum total cholesterol, LDL cholesterol, apo-lipoprotein B and triglyceride levels, by ingesting MP-T3 and compositions thereof, thereby reducing serum total cholesterol, LDL cholesterol, apo-lipoprotein B and triglyceride levels.

Embodiments of the invention relate to methods for increasing the HDL/LDL cholesterol ratio in mammalian serum, by ingesting a stabilized MP-T3 derivative such as, lactoferrin blended with palm T3 and mixtures thereof, thereby increasing the HDL/LDL ratio.

Tocotrienols (T3)

Embodiments of the invention pertain to synergistic admixtures of metallo-proteins (MP) and tocotrienols (T3). Such MP-T3 mixtures contain at least one MP compound (an active ingredient) and at least one T3 (a second active ingredient) that are blended, suspended or dissolved in a carrier to provide increased bioavailability and stability for both the active ingredient(s), in particular, for the T3 compounds.

An admixing of at least one MP compound, such as lactoferrin, effectively increases the stability and functionality of T3 in a biological source by one or a combination of the following: (i) by blocking antagonistic effects of metals such as iron, copper and zinc that are capable of degrading T3 compounds in the formulation or biological milieu; ii) by increasing the transport of T3 compounds across the intestinal mucosa into the blood stream via specific receptor-mediated pathways. As a result, T3 and T3-like compounds in formulations as described herein may be more bio-available than the corresponding non-stabilized T3 forms.

"T3 and T3-like" compounds are defined in U.S. Pat. No. 5,591,772; U.S. Pat. No. 5,821,264, U.S. Pat. No. 6,204,290 and U.S. Pat. No. 6,239,171, which are incorporated herein by reference. In brief, T3 and T3-like compounds of this invention are characterized by specific structural characteristics and specific biological activity or, alternatively, by specific high performance liquid chromatography ("HPLC") elution profiles and specific biological activity. More particularly, the compounds of this invention may be characterized by three structural features: (1) a hydrogen donor group (or a group which can be hydrolyzed to a hydrogen donor group) attached to an aromatic ring system, (2) an atom having at least one lone pair of electrons, said electrons being in conjugation with the aromatic system and (3) a side chain comprising one or more isoprenoid or isoprenoid-like units attached to a position adjacent to that atom. Also encompassed are the hydrolysis and oxidation products obtained from such compounds. In addition, T3 and T3-like compounds having the above-mentioned structural characteristics are also characterized by the ability to inhibit the activity of β-hydroxy-β-methyl glutaryl coenzyme A (HMG-CoA) reductase. Furthermore, these compounds are effective in the treatment or prevention of one or more of the following diseases or conditions: hypercholesterolemic diseases, thrombotic diseases, oxidative conditions, inflammation or immunoregulatory diseases or, alternatively, in increasing feed conversion efficiency.

This invention encompasses the five known naturally occurring T3 compounds, including but not limited to T3, alpha-T3, beta-T3, gamma-T3 and delta-T3. This invention further includes the D- or L-isomer and the D, L-racemic mixture of each T3 and T3-like compounds. However, the naturally occurring D-isomer is preferred.

In preferred embodiments, the T3 and T3-like compounds may be obtained from any biological materials including, but not limited to, oats, wheat, rye, barley, soybean, wheat germ, wheat bran, corn, rice (including whole kernel, husk or hull, endosperm and germ), cottonseed, milkweed, flax, sesame, rice bran, parboiled brown rice, brown rice flour, olives, vegetable oil distillate, fruit concentrate evaporate, barley bran, palm oil, wheat germ oil, rice bran oil, barley oil, coconut oil, cottonseed oil, soybean oil, other cereal grains and other cereal grain oils, plant tissues, flowers, bushes (such as juniper), trees (such as pine and rubber), fruits (such as melons, berries, tomatoes and citrus fruits), vegetables, grasses (such as alfalfa), fungi (such as mushrooms), leaves, seeds (such as sesame, millet and pine), stems, bark, roots, nuts (such as cashews and almonds) and legumes (such as peanuts), or portions thereof.

Toxicological and pharmacological studies show that supplementation with palm T3 up to 2,500 milligrams per day per kilogram of body weight does not produce any significant side effects. And surely, for most therapeutic and health maintenance purposes, lower concentrations are sufficient and generally preferred. Although higher levels can be used for therapeutic purposes, those who want to enhance their antioxidant intake can use 30 to 50 milligrams of T3 daily.

Dosages for administration of T3s range from about 1 to about 1200 mg/day, commonly from about 1 to about 100 mg/day, and typically from about 1 to about 60 mg/day. Generally, in terms of patient body weight, usual dosages range from about 0.01 to about 20 mg/kg/day, commonly from about 0.01 to about 2.0 mg/kg/day, typically from about 0.01 to about 1.0 mg/kg/day. However, in the therapeutic and prophylactic formulations of the claimed invention, higher concentrations may be used such as 10-1000 mg of T3 per day, more preferably 25-250 mg of T3 per day.

Metallo-Proteins (MPS)

In preferred embodiments, the 'metallo-protein (MP)' includes proteins such as lactoferrin (LF), transferrin, ovo-transferrin (conalbumin) (OTF), ceruloplasmin, metallothionein, Angiogenin (ANG) their complexes or combinations thereof. Preferably, the MPs suitable for the preparation of T3 mixtures are lactoferrin, ovo-transferrin their complexes or combinations thereof. A most preferred MP suitable for the present invention is lactoferrin and lactoferrin complexes with angiogenin (ANG). "Metallo-protein complex" as the term is used herein means a composition which includes at least one metallo-protein.

In some preferred embodiments, the "metallo-protein complex" includes stabilizing components such as one or more polysaccharide substrates as described in U.S. Pat. No. 6,172,040 which is incorporated herein by reference. More preferably, the polysaccharides include galactose-rich polysaccharide (GRP), sulfated glycosamino glycans (GAG), carrageenans, and/or oligosaccharides. Yet more preferably, the polysaccharide substrate includes a galactose-rich polysaccharide (GRP) substrate which is extracted from agar and/or agarose and includes galactose derivatives such as anhydrogalactose, 2-O-methyl galactose, 4-O-methyl galactose or combinations thereof.

Yet more preferably, the polysaccharide substrate includes a sulfated glycosaminoglycan (GAG) substrate which includes heparin, heparan sulfate and/or mucins.

Yet more preferably, the polysaccharide substrate includes a carrageenan substrate which includes Satiagel® brands (Degussa) ADG-14 (kappa/iota-type), ADF-23 (kappa/iota-type), DF-52 (iota-type); Genulacta® brand (Hercules) IM K-100 (kappa-type); and/or Carravisco® brand DFL-1 (lambda-type).

The polysaccharide substrate may include an oligosaccharide substrate such as celluloses, hemi-celluloses, both short- and long-chain fructooligosaccharides (FOS) and/or pectins.

The substrate may be combined with the metallo-protein by mixing the substrate and the metallo-protein in a liquid medium. The attachment of the metallo-protein to the substrate may be non-covalent or covalent. The interaction may be at the N-terminus, the C-terminus or any molecular region, but preferably the N-terminus of the metallo-protein. In other embodiments, the complex is formed by a non-covalent association between the metallo-protein and the carbohydrate molecule. The basis of the association may be electrostatic or by hydrophobic interaction or using bifunctional reagents.

In some embodiments, the "metallo-protein complex" includes a mixture of immobilized and free (non-immobilized) metallo-protein. In some embodiments, other metallo-proteins are included. In a most preferred embodiment, the "metallo-protein complex" includes both LF and ANG either as free or immobilized forms or a mixture of free and immobilized forms or LF and ANG may be stabilized by association to each other.

Lactoferrin

Lactoferrin (LF) is a metal-binding glycoprotein that plays a key role in the chelation and physiological management of divalent cations, especially iron levels in the body. Accordingly, LF is equipped with unique molecular structure and a classic functional mechanism for high-affinity binding of iron, zinc, copper, manganese, chromium, aluminum, and gallium. Apart from its role as a physiological transport molecular system, LF also elicits a powerful protective role in the intestinal tract by eliminating harmful pathogens, toxic chemicals, heavy metals, and free radicals. Specific receptors in the human duodenal brush border are involved in promoting LF interaction and function during the elemental absorption and nutrient transport. These LF-binding receptors exist relatively at a high density (about 4 billion sites/microgram) on the human intestinal brush-border membrane to facilitate uninterrupted active transport and processing of nutrients into the circulatory system. (Naidu A S. Lactoferrin—Natural Multifunctional Antimicrobial, CRC Press/Boca Raton, pp. 1-86, 2000; Cox R et al. *Biochem Biophys Acta* 588:120-8, 1979; Kawakami H, Lonnerdal B, *Am J Physiol* 261:G841-6, 1991).

As used herein, "lactoferrin", or "LF" refers to various protein preparations and forms, including but not limited to, lactoferrin-(tcr) (as described in Naidu U.S. Pat. No. 7,125, 983), freely-dispersed native (fdn)-lactoferrin which includes partially saturated and metal-free (apo) forms of LF. The term LF further refers to fully and partially glycosylated polypeptide chains of LF, incomplete polypeptide chains including half-molecules comprising C- and N-terminus lobes of LF. The term LF categorically excludes aggregated-LF and immobilized (Im)-LF forms (as described in Naidu U.S. Pat. No. 6,172,040 B1) that are devoid of any (fdn)-LF.

In the present invention, the effective amounts of LF in a MP-T3 (LF-T3) mixture may range from about 1 mg to 5000 mg by weight, preferably about 10 mg to 1000 mg by weight and most preferably about 25 mg to 250 mg by weight.

Compositions

The MP-T3 compositions compositions described herein are generally administered 1-5 times daily, more preferably, 2-3 times daily. Dosage amounts of MP-T3 compositions and intervals can be adjusted individually to provide plasma levels of the active ingredient(s) which are sufficient to maintain the cholesterol management or lowering effects desired.

The MP-T3 compositions of the present invention can prevent high serum lipid and cholesterol levels in a mammal, including humans, thereby lowering the risks of developing obesity and cardiovascular disease.

The MP-T3 mixtures and formulations described herein are useful in pharmaceutical compositions, foodstuffs and dietary supplements. Advantageously, these products can be used as hypocholesterolemic, antithrombotic, antioxidant, antiatherogenic, anti-inflammatory and immuno-regulatory agents.

The MP-T3 compositions may take the form of tablets, capsules, emulsions, suspensions and powders for oral administration, sterile solutions or emulsions for parenteral administration, sterile solutions for intravenous administration and gels, lotions and cremes for topical application. The MP-T3 compositions may be administered to humans and animals in a safe and effective amount to elicit any of the desired results indicated for the compounds and mixtures described herein.

The MP-T3 compositions of this invention typically comprise a physiologically effective amount of an acceptable carrier. Such carriers may be solid or liquid, such as, for example, cornstarch, lactose, sucrose, olive oil or sesame oil. If a solid carrier is used, the dosage forms may be tablets, capsules or lozenges. Liquid dosage forms include soft gelatin capsules, syrup or liquid suspension.

Optional Active Ingredients

MP-T3 formulation may include optionally one or more bio-active agents, such as an angiogenic factors, phytosterols, coenzyme Q10, nattokinase, their derivatives or combinations thereof.

Embodiments of the invention relate to compositions that also include an agent that promotes angiogenesis and/or vasculogenesis. In preferred embodiments, the agent to support angiogenesis and/or vasculogenesis is ANG, ANG-derived compounds or ANG-complexes (ANGex) described in U.S. patent application Ser. No. 11/734,711 and U.S. Pat. No. 7,601,689 which are incorporated herein by reference. ANGex refers to angiogenin covalently or non-covalently complexed with other compounds such as proteins, polysaccharides, cellulose compounds, nucleic acids, nucleotides, lipids and metallic compounds. Effective amounts of ANG, ANG-derived compounds or ANGex in the formulation reinforce the cardiovascular framework.

Angiogenin (ANG) has been shown to be a key mediating factor in the underlying cascade of chemical events leading to angiogenesis, which makes it a very important precursor molecule for both muscle development and vascular generation. The actions of ANG involve nearly all phases of angiogenesis (Strydom D J. *Cell Mol. Life Sci.* 54:811-824, 1998; Acharya B et al., *Proc. Natl. Acad. Sci.* USA 91:2915-2919, 1994).

As used herein, "angiogenin" or "ANG" refers to an angiogenic-stimulating factor, which is a 14-kDa heparin-binding protein that occurs in most cells, and is also present in various biological fluids such as plasma and milk.

Suitable ANG can be isolated from dairy sources including colostrum, milk, whey and milk serum from humans, cows, buffalos, horses, sheep, pigs or camels. Additionally, ANG also can be purified from other biological fluids from animals (eg. blood), recombinant sources and genetically-modified organisms (GMOs). Recombinant ANG may be cloned-expressed in either prokaryotic or eukaryotic cellular systems. ANG is isolated by any conventional method, such as by filtration methods, chromatography techniques using ion-exchanger, molecular-sieve or affinity columns.

ANG-Derived Compounds and ANGex

ANG-derived compounds and ANGex (as described in US Patent Publication Nos. 2008/0254018 and U.S. Pat. No. 7,601,689, both of which are incorporated herein by reference) may be substituted for ANG for any treatment for which ANG is useful. ANG-derived compounds and ANGex bring the added benefits of increased stability for ANG as an active agent. Because of the increased stability, ANG-derived compounds and ANGex demonstrate an increased residence time compared to ANG so that both dosage and frequency of administration is less than with ANG.

Dietary supplementation with ANG, ANG-derived compounds or ANGex may be helpful to individuals suffering from vascular disorders such as congestive heart failure, myocardial infarction, stroke, stable and unstable angina, poor circulation, for supportive supplementation of long-term medications in the management of hypertension, hyperlipidemia, diabetes, and chronic fatigue syndrome; mitochondrial diseases including mitochondrial encephalomyopathy, lactic acidosis, and stroke-like symptoms, Kearns-Sayre syndrome and Alpers' disease.

Some embodiments include immobilized ANG complexes (ANGex) and mixtures of ANGex and free dispersed native (fdn)-ANG having preserved, enhanced and specific biological activity. ANG is immobilized on naturally occurring substrates, preferably via the N-terminus region of the ANG by covalent attachment. Suitable substrates include proteins, polysaccharides, cellulose compounds, nucleic acids, nucleotides, lipids and metallic compounds. Preferred substrates include collagen, gelatin, fibronectin, casein, mucin, heparin-sulfate, carrageenan, gums/galactans, pectins, deoxyribonucleic acid, adenosine triphosphate or a triglyceride. Galactose-rich polysaccharide (GRP), vitamin-E, ceruloplasmin and lactoferrin (LF) being most preferred. In some embodiments, ANGex is prepared by mixing ANG with the substrate material.

In the present invention, the effective amounts of ANG, ANG-derived compounds or ANGex in a MP-T3 composition may range from about 0.01 mg to 1000 mg by weight, preferably about 0.1 mg to 100 mg by weight and most preferably about 1 mg to 10 mg by weight.

Phytosterols

Phytosterols and fiber facilitate cholesterol sequestration from the body through increased excretion of bile salts and bile acids, resulting in lower levels of circulating cholesterol. The effect of soluble fiber in cholesterol management is well documented in the literature.

The combination of phytosterols with a flavone and/or fiber with MP-T3 is an effective way to reduce cholesterol. Accordingly, MP-T3 formulations of the present invention can further include one or more phytosterol or fiber or derivatives thereof.

Phytosterols are plant sterols found, for example, in small amounts in vegetable oils such as corn, bean, or other plant oils, where they occur as free sterols, fatty acid esters, and glycosides. A number of different phytosterol structures are found in nature. The most common of these structures are campesterol, beta-sitosterol, and stigmasterol.

Phytosterols are structurally similar to cholesterol, the main differences occurring in the carbon skeleton of their side chains. Because cholesterol and phytosterol molecules are similar, the human body does not differentiate between the two molecules. Therefore, phytosterols compete with cholesterol for absorption in the small intestine but the phytosterols are not absorbed by the body.

Cholesterol is absorbed in the upper third of the intestine. Phytosterols block the absorption of dietary cholesterol into the bloodstream and inhibit the re-absorption of cholesterol from bile acids in the digestive process, thus reducing the amount of cholesterol entering the bloodstream. The absorption rate of phytosterols is approximately $\frac{1}{10}^{th}$ that of cholesterol, meaning that the pathways in the intestine are occupied by phytosterols for an extended period of time, which makes the blocking process even more effective.

A method of reducing cholesterol in the bloodstream by administering beta-sitostanol with campestanol in defined ratios as fatty acid esters derived from vegetable oils is disclosed in WO 98/06405. Furthermore, U.S. Pat. No. 5,502,045 discloses the reduction of cholesterol absorption into the bloodstream by administering beta-sitostanol derived from vegetable oils.

In some embodiments, between about 10 milligrams and 5000 milligrams of a phytosterol is included in a MP-T3 formulation of this invention, preferably between about 50 milligrams and 2500 milligrams, on a weight basis.

Glucomannan

Glucomannan is a polysaccharide derived from tubers of konjac plant (*Amorphophallus konjac*). Like many soluble fibers, glucomannan binds to a variety of substances in the gut to slow digestion, relieve constipation and reduce the absorption of fat and carbohydrates. It helps in weight loss, improves lipid profile as well as glucose tolerance in obese individuals. Glucomannan could also reduce total serum cholesterol in healthy individuals and in adults with overweight and diabetes. These activities are reportedly due to inhibition of active transport of cholesterol in the jejunum and absorption of bile acids in the ileum.

In some embodiments, between about 100 milligrams and 10,000 milligrams of glucomannan fiber is included in a MP-T3 formulation of this invention, preferably between about 500 milligrams and 2500 milligrams, on a weight basis.

Coenzyme Q-10

Coenzyme Q-10 (CoQ-10) is fat-soluble quinine, structurally similar to vitamin K and is found in most living organisms. CoQ-10 is essential for the production of cellular energy. Due to its involvement in the ATP synthesis, CoQ-10 affects almost every cellular function of the body, which makes this molecule essential for the health. CoQ-10 particularly affects those systems that are the most metabolically active such as the heart, immune system, gingiva, and gastric mucosa The benefits of CoQ-10 supplementation are compelling in the protective and therapeutic management of cardiovascular health. Several controlled studies have reported the clinical efficacy of CoQ-10 as a supplemental therapeutic in the treatment of congestive heart failure (CHF). Myocardial tissue levels of CoQ-10 in CHF patients is about 33% lower than control subjects. Accordingly, the severity of symptoms associated with CHF and the presence of dilated cardiomyopathy strongly correlate with the degree of CoQ-10 deficiency. (Mortensen S A. *Clin Investig* 71:S116-123, 1993).

Another widespread replenishment of CoQ-10 is in the clinical management of hypertension associated with deficiencies of succinate dehydrogenase and CoQ-10 reductase activity. Accordingly, reversal of CoQ-10 deficiency by dietary replenishment seems to control hypertension with reductions in systolic and diastolic blood pressure. (Greenberg S, Frishman W H. *J Clin Pharmacol* 30:596-608, 1990; Yamagami T, et al. *Res Commun Chem Pathol Pharmacol* 14:721-727, 1976).

Yet another common application of CoQ-10 is as an active adjuvant to rectify (balance) coenzyme deficiency that builds-up during long-term usage of certain medications. Lipid-lowering drugs ("statins") such as lovastatin, simvastatin, pravastatin and gemfibrozil cause a decrease in serum CoQ-10 levels, which might predispose serious cardiovascular conditions. Therefore, it is advisable to use CoQ-10 supplement with prescription of statins, to protect individuals from risks associated with cardiac dysfunction. Beta-blockers (drugs that slow down heart rate and lower blood pressure) could also decrease the endogenous CoQ-10 levels by inhibition of CoQ-10-dependent enzymes. Also, certain oral hypoglycemic agents such as glyburide, acetohexamide, and tolazamide could decrease plasma CoQ-10 levels. CoQ-10 supplementation has been reported to reduce insulin requirements in diabetes mellitus. Therefore, diabetic patients taking CoQ-10 might require dosage adjustments of hypoglycemic agents. [Kaikkonen J, et al. *FEBS Lett* 443:163-166, 1999; Thibault A, et al. *Clin Cancer Res* 2:483-491, 1996; Pepping J. *Am J Health-System Pharm* 56:519-521, 1999; Kishi T, et al. *J Med* 7:307-321, 1976).

US Patent Application 20060269535 which is incorporated herein by reference, teaches methods to prepare specific combinations of CoQ-10 mixtures to trigger the release of bioenergy (bio-E) in the form of adenosine triphosphate (ATP).

Additionally the invention discloses compositions of functional delivery systems to recreate physiological proton gradients for rapid activation and release of cellular and extracellular ATP.

US Patent Application 20070253941 which is incorporated herein by reference describes methods to enhance the bioavailability of CoQ-10, and supporting the cardiovascular system, and a composition including CoQ-10, lactoferrin and/or angiogenin for use in the described methods, for multifunctional health applications.

CoQ-10 analogs include reduced, semi-reduced CoQ-10 and other ubiquinone derivatives described, for example, in WO 8803015, the teachings of which are incorporated herein by reference.

In some embodiments, between about 10 milligrams to 500 milligrams of CoQ-10 or an analog is included in a MP-T3 composition of the invention, preferably between about 25 to 250 milligrams, on a weight basis.

Nattokinase

Nattokinase, also called Substilisin NAT (EC 3.4.21.62 and CAS Registry Number 9014-01-1), is a pro-fibrinolytic enzyme present in a vegetable cheese-like food called 'Natto', extremely popular in Japan and has been consumed for over 1,000 years. Natto is prepared by fermenting boiled soybeans with Bacillus spp. (e.g., Bacillus subtilis in particular Bacillus subtilis var. natto). Nattokinase is a 381 amino acid pro-enzyme that is cleaved to generate a 275 amino acid form with a molecular weight of about 27.7 kDa. Nattokinase has fibrinolytic activity in vitro and in vivo. Oral administration of nattokinase could be beneficial for treating hypertension and reducing thrombosis.

U.S. Pat. No. 7,014,851 discloses a food supplement effective for inhibiting platelet aggregation with nattokinase as an active ingredient and has Bacillus natto culture extract, containing a high proportion of nattokinase containing 1 μg/g or less of vitamin K2 on a dry weight basis, as an active ingredient.

U.S. Pat. No. 7,041,286 discloses a nattokinase composition for mitigating adverse effects of an imminent or actually-occurring pernicious thrombotic event, such as a heart attack or stroke, in the person.

US Patent Application 20070116699 discloses a nattokinase composition for reducing whole blood viscosity in individuals having or at risk for vascular diseases.

In some embodiments, between about 50 to 50,000 FU (enzymatic units) of nattokinase is included in a MP-T3 composition of the invention, preferably between about 500 to 5000 FU, on an enzymatic activity basis.

MP-T3 formulations of the present invention may even further include optionally one or more antioxidant agents, phytoceutical agents, lipid lowering pharmaceutical agents (such as statins), their derivatives or combinations thereof.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and tocopherols and beta-carotene; natural components such as camosol, camosic acid and rosmanol found in rosemary and hawthorn extract, proanthocyanidins such as those found in grapeseed or pine bark extract, and green tea extract.

Alpha-Tocopherol (α-Tocopherol)

Alpha-tocopherol (α-tocopherol) is the name of the most active form of vitamin E in humans. It is also a powerful biological antioxidant.

Vitamin E may help prevent or delay coronary heart disease by limiting the oxidation of LDL-cholesterol. Vitamin E also may help prevent the formation of blood clots, which could lead to a heart attack. Observational studies have associated lower rates of heart disease with higher vitamin E intake. A study of approximately 90,000 nurses suggested that the incidence of heart disease was 30% to 40% lower among nurses with the highest intake of vitamin E from diet and supplements. Researchers found that the apparent benefit was mainly associated with intake of vitamin E from dietary supplements. (Jialal I, Fuller C J. Can J Cardiol 11:97-103, 1995).

In some embodiments, between about 50 to 5000 IU of tocopherol or an analog is included in a MP-T3 composition of the invention, preferably between about 250 to 1000 IU, on an activity basis.

Glutathione (GSH)

Glutathione (GSH) is a compound classified as a tripeptide made of three amino acids: cysteine, glutamic acid and glycine. Glutathione is also found in every part of the body, especially the lungs, intestinal tract, and liver. Fish oil, riboflavin (vitamin B2), vitamin C, and selenium also encourage the production and absorption of GSH. In fact, without selenium the body cannot produce glutathione.

The body produces and stores the largest amounts of GSH in the liver, where it is used to detoxify harmful compounds so that they can be removed from the body through the bile. The liver also supplies GSH directly to red and white blood cells in the bloodstream; it helps keep red blood and white blood cells healthy to maximize the disease-fighting power of the immune system. Glutathione also appears to have an anti-aging affect on the body. GSH levels decline with age, and a lack of glutathione has been shown to leave the body more vulnerable to damage by free radicals, thus speeding up oxidation (wearing down) of the body.

In some embodiments, between about 10 milligrams and 1000 milligrams of GSH is included in a composition of the invention, preferably between about 50 milligrams and 500 milligrams on a weight basis.

Astaxanthin

Astaxanthin is a carotenoid (like beta-carotene), a long chain molecular pigment, that is extracted from a tropical microalgae (Haematococcus pluvialis). It is the molecule that gives color to salmon and some crustaceans. It has 500 times the antioxidant potency of vitamin E and 10 times the activity of beta-carotene.

Astaxanthin exhibits strong free radical scavenging activity and protects against lipid peroxidation and oxidative damage of LDL-cholesterol, cell membranes, cells, and tissues. Oxidized LDL-cholesterol is implicated in the formation of plaques inside arteries that lead to heart disease, blood clots and strokes. Studies have revealed that astaxanthin reduces the amount of inflammation-induced cardiac cell death that occurs whenever a blood clot blocks the blood supply to an area of the heart.

Because astaxanthin crosses the blood-brain barrier, it is found to reduce the effects of free radicals in the brain which cause progressive cell damage and neurological dysfunction. Astaxanthin has been shown to be extremely neuron-protective. This substance provides brain health.

In some embodiments, between about 0.1 milligrams and 100 milligrams of Astaxanthin is included in a composition of the invention, preferably between about 1 milligram and 10 milligrams on a weight basis.

Grape Seed Extract

Grape seed extract includes specialized flavonoids called oligomeric proanthocyanidins (OPCs). Studies suggest grape seed helps improve blood circulation, prevent atherosclerosis, lowers blood pressure and decreases low density lipoprotein cholesterol levels and increases high density lipoprotein levels.

The OPCs are chemically known as flavonoids or polyphenols, which can differ substantially based on their polymer arrangement. For example, polyphenols can exist in single (monomers), double (dimers), triple (trimers), quadruple (tetramers) and even longer cyanidin chains (tannins). Any chain length containing from about 2-7 monomers is referred to as an oligomer and longer chains are generally referred to as polymers.

In some embodiments, between about 10 milligrams and 1000 milligrams of grape seed extract is included in a composition of the invention, preferably between about 50 milligrams and 500 milligrams on a weight basis.

Pine Bark Extract

Pine bark extract can be included in the compositions of the invention to reduce low density lipoproteins and to help strengthen blood vessel walls. Pine bark extract is also known as French Marine Pine Bark Extract, French Maritime Pine Bark Extract, Leucoanthocyanidins, OPC, Oligomeric Proanthocyanidins, PCO, Pine Bark, *Pinus maritima, Pinus pinaster*, Procyandiol Oligomers, Procyanodolic Oligomers, Pycnogenol, and Pygenol.

In some embodiments, between about 100 milligrams and 500 milligrams of pine bark extract is included in a composition of the invention, in particular, between about 50 milligrams and 250 milligrams on a weight basis.

Polymethoxylated flavones, polycosinol, red yeast rice, and gugulipid are additional active ingredients that can be used in the present formulations to treat one or more of the ailments, including lowering cholesterol, indicated within the present specification.

Polymethoxylated Flavones

Polymethoxylated flavones (PMFs) suitable for the present invention include but not limited to tangeretin and nobiletin, found in tangerines sweet orange peel (*Citrus sinesis*) and bitter orange peel (*Citrus aurantium*). Suitable examples of polymethoxylated flavones that are citrus flavonoids include tangeretin and nobiletin.

Dosages for administration of naturally-occurring polymethoxyflavones range from about 1 to 1000 mg/day, preferably from about 5 to 500 mg/day, and more preferably from about 10 to about 100 mg/day.

Policosanol

Policosanol consists of a mixture of fatty alcohols derived from waxes of sugar cane (the main source of policosanol,) yams, and beeswax. The main ingredient of policosanol is octanosol. These active substances act to lower cholesterol levels by several mechanisms which include blocking the formation of cholesterol in the liver.

Not to be limited by theory, it is believed that the alcohols in policosanol act on cholesterol metabolism in the liver, but at a different part of the metabolic pathway than statins. Many animal studies with policosanol demonstrate a cholesterol lowering effect, and more recently human studies have suggested that LDL cholesterol can be reduced to a degree similar to that achieved with statins, and that HDL cholesterol can be increased by as much as 10-25% (an effect difficult to achieve with statins). Policosanol also reduces the platelet aggregation (i.e., the "stickiness" of platelets, the blood elements that promote blood clotting).

In some embodiments, between about 1 milligrams and 100 milligrams of policosanol is included in a composition of the invention, preferably between about 5 milligrams and 50 milligrams, and more preferably between about 10 milligrams and 25 milligrams on a weight basis.

Red Yeast Rice (Extract)

Red yeast rice (extract) is an Asian dietary staple made by fermenting red yeast (*Monascus purpureus*) on rice and is recognized as a cholesterol-lowering agent. This is due in part to a careful fermentation process that yields statins, compounds known to reduce cholesterol levels.

As a substance, red yeast rice extract has a number of heart-healthy benefits. It helps reduce total cholesterol levels, lower levels of LDL cholesterol, increase levels of HDL cholesterol, and lower levels of triglycerides. Not to be limited by theory, it appears that red yeast rice (and its extracts) accomplishes this by restricting the liver's production of cholesterol. The compound responsible for this effect, mevinolin, is chemically identical to the cholesterol lowering compound known as lovastatin, which is sold as the prescription drug Mevacor. Additionally, unsaturated fatty acids in red yeast rice extract are also believed to be beneficial, possibly by lowering triglycerides.

In some embodiments, between about 50 milligrams and 5000 milligrams of red yeast rice extract is included in a composition of the invention, preferably between about 100 milligrams and 1000 milligrams on a weight basis.

Artichoke (Extract)

Artichoke extract has been shown to lower cholesterol and also improve the ratio of protective HDL to LDL cholesterol. Without intending to be limited by theory, artichoke extract is believed to lower cholesterol levels by increasing the flow of bile from the gallbladder. Bile plays a key role in the excretion of excess cholesterol from the body.

In some embodiments, between about 50 and 1000 milligrams of artichoke extract is included in a composition of the invention, preferably, about 150 to 700 milligrams. In preferred embodiments, administration is 1-5 times daily, preferably 2-3 times daily.

Gugulipid

Gugulipid is an extract from the mukul myrrh tree (*Commiphora mukul*) that is native to India. It is a purified extract standardized for compounds known as guggulsterones. The active compounds in gugulipid believed to be responsible for the cholesterol-lowering properties are two steroids: E- and Z-guggulsterone. Several clinical studies have shown gugulipid has an ability to lower both cholesterol and triglyceride levels.

The mechanism of action for gugulipid's cholesterol lowering action is its ability to increase the liver's ability to break down cholesterol. The dosage of gugulipid is based on its guggulsterone content.

Related benefits are its ability to prevent plaque from forming in arterial walls, which can lead to heart attacks if unchecked. Moreover, it acts as an anti-coagulant by inhibiting blood platelets from clumping together, and, therefore, affords protection against blood clots. Gugulipid also harbors antioxidant properties.

In some embodiments, between about 10 milligrams and 1000 milligrams of gugulipid is included in a composition of the invention, preferably between about 100 milligrams and 500 milligrams on a weight basis.

Statins

The statins (or HMG-CoA reductase inhibitors) form a class of hypolipidemic drugs used to lower cholesterol levels in people with or at risk of cardiovascular disease. They lower cholesterol by inhibiting the enzyme HMG-CoA reductase, which is the rate-limiting enzyme of the mevalonate pathway of cholesterol synthesis. Inhibition of this enzyme in the liver stimulates LDL receptors, resulting in an increased clearance of low-density lipoprotein (LDL) from the bloodstream and a decrease in blood cholesterol levels. The first results can be seen after one week of use and the effect is maximal after four to six weeks.

LDL-lowering potency varies between agents. Cerivastatin is the most potent, followed by (in order of decreasing potency) rosuvastatin, atorvastatin, simvastatin, lovastatin, pravastatin, and fluvastatin. (Shepherd J, et al. *Am J Cardiol* 91 (5): 11-17, 2003).

Additional active ingredient(s) that can be included in the formulation include cholesterol lowering drugs including, but not limited to cholestyramine, colestipol, clofibrate, colesevelam (WelChol®), gemfibrozil, fenofibrate (Tricor®), Ezetimibe (Zetia®), Lovastatin (Mevacor®), Simvastatin (Zocor®), Pravastatin (Pravachol®), Fluvastatin (Lescol®), Rosuvastatin Calcium (Crestor®), Atorvastatin (Lipitor®) or combinations thereof.

Synergistic Agents

MP-T3 formulations of the present invention may further include optionally one or more agents that affect cholesterol metabolism, such as amino acids, vitamins, minerals, their derivatives or combinations thereof.

Prior art describes several factors that promote T3 activity in a synergistic manner. The additive or synergistic influencing factors include amino acids such as arginine and carnitine; and trace elements such as magnesium, calcium and chromium. (Hayashi T, et al. *Proc Natl Acad Sci USA* 102:13681-13686, 2005).

Although these amino acids are usually obtained through food or synthesized by the body, a dietary supplementation in combination with MP-T3 could provide synergistic health benefits.

Arginine

Arginine supplementation can help individuals with high serum levels of cholesterol. Although the exact mechanism is unknown, human clinical studies have indicated that arginine could lower LDL and total cholesterol levels.

In some embodiments, between about 50 to 1000 milligrams of arginine is included in a composition of the invention, preferably between about 100 mg to 500 mg, on a weight basis.

Carnitine

Carnitine produced by the liver and derived from the amino acids methionine and lysine, may possess cholesterol-lowering benefits. Carnitine plays an important role in transporting long-chained fatty acid across the mitochondrial membranes in the cell in order to produce energy. Carnitine is often used for heart conditions and it may be helpful to treat angina or chest pain. Carnitine is also effective in the treatment of congestive heart failure, to reduce cholesterol (LDL), increase high density lipoprotein (HDL), and for intermittent claudication. (Bell F P, et al. *Comp Biochem Physiol* 87:587-591, 1987).

Carnitine and carnitine analogs include, but not limited to racemic or essentially pure L-carnitine (carnitine), or a corresponding alkanoyl-carnitine such as e.g. acetyl-carnitine or propionyl-carnitine, or a suitable salt of such compounds such as e.g. L-carnitine tartrate, L-carnitine fumarate, L-carnitine-magnesium-citrate, acetyl-L-carnitine tartrate, acetyl-L-carnitine-magnesium-citrate, or any mixture of the afore mentioned compounds.

In some embodiments, between about 10 milligrams to 1000 milligrams of carnitine is included in a MP-T3 composition of the invention, preferably between about 100 mg and 500 milligrams, on a weight basis.

Certain B-vitamins, in particular B3 (nicotinic acid) and B5 (pantothenic acid) play a critical role in the cholesterol biosynthesis pathways, and therefore, could serve as powerful synergists with MP-T3 formulations of the present invention.

Niacin or Nicotinic Acid

Niacin or nicotinic acid, one of the water-soluble B vitamins, improves all lipoproteins when given in doses well above the vitamin requirement. Nicotinamide, another form of the vitamin niacin, does not lower cholesterol levels and should not be used in the place of nicotinic acid.

Niacin has been widely used as a pharmacologic agent to regulate abnormalities in plasma lipid and lipoprotein metabolism and in the treatment of atherosclerotic cardiovascular disease. Although the use of niacin in the treatment of dyslipidemia has been reported as early as 1955, only recent studies have yielded an understanding about the cellular and molecular mechanism of the action of niacin on lipid and lipoprotein metabolism. In brief, the beneficial effect of niacin to reduce triglycerides and apolipoprotein-B containing lipoproteins (e.g., VLDL and LDL) are mainly through: a) decreasing fatty acid mobilization from adipose tissue triglyceride stores, and b) inhibiting hepatocyte diacylglycerol acyltransferase and triglyceride synthesis leading to increased intracellular apo B degradation and subsequent decreased secretion of VLDL and LDL particles. The mechanism of action of niacin to raise HDL is by decreasing the fractional catabolic rate of HDL-apo AI without affecting the synthetic rates. Additionally, niacin selectively increases the plasma levels of Lp-AI (HDL subfraction without apo AII), a cardio-protective subfraction of HDL in patients with low HDL.

Nicotinic acid reduces LDL-cholesterol levels by 10 to 20 percent, reduces triglycerides by 20 to 50 percent, and raises HDL-cholesterol by 15 to 35 percent. Patients on nicotinic acid are usually started on low daily doses and gradually increased to an average daily dose of 1.5 to 3 grams per day.

In some embodiments, between about 2 to 200 milligrams (10% to 1000% DV) of niacin is included in a MP-T3 composition of the invention, preferably between about 10 to 100 milligrams (50% to 500%), on a weight basis.

Pantethine

Pantethine is a combination of pantothenic acid (vitamin B-5) and beta mercaptoethylamine. Pantethine is the precursor to coenzyme A, the critical intermediate in Kreb's Cycle for cellular energy production.

Pantethine is found naturally in small quantities in most forms of life, and therefore, in food sources. Pantethine has been found to decrease serum levels of total cholesterol, low-density lipoprotein cholesterol (LDL-C), apolipoprotein B and triglycerides. It has also been found to increase high-density lipoprotein cholesterol (HDL-C) and apolipoprotein A1 levels. In isolated hepatocytes, pantethine has been shown to inhibit both cholesterol and fatty acid synthesis. It is believed that pantethine, by acting as a precursor of coenzyme A, may enhance the beta-oxidation of fatty acids.

In some embodiments, between about 1 to 100 milligrams (10% to 1000% DV) of pantethine is included in a MP-T3 composition of the invention, preferably between about 5 to 25 milligrams (50% to 250%), on a weight basis.

Non-limiting examples of minerals include magnesium, calcium, chromium, selenium, and derivatives thereof or combinations thereof. Preferably, minerals are provided in appropriate salt forms. In a most preferred embodiment, the metals are provided as covalently bound to MP. When complexed with MP, the metal is in a bio-available form that can be used by the body.

Magnesium

Magnesium ($Mg^{+2}$) is the controlling factor for the rate-limiting enzyme HMG-CoA in the cholesterol biosynthesis. Biosynthesis of cholesterol is essential for hormone synthesis, and membrane maintenance. This is achieved via a series of enzymatic reactions that convert HMG-CoA to cholesterol. The rate-limiting reaction of this pathway is the enzymatic conversion of HMG CoA to mevalonate via HMG CoA Reductase. The statin drugs and Mg (II) inhibit this critical enzyme.

Several human clinical trials have shown that statins, when administered to subjects with high LDL-cholesterol values, lowers its blood levels 35 to 65%. They also reduce the incidence of heart attacks, angina and other non-fatal cardiac events, as well as cardiac, stroke, and total mortality. These effects of statins derive less from their lowering of LDL cholesterol than from their reduction of mevalonate formation which improves endothelial function, inhibits proliferation and migration of vascular smooth muscle cells and macrophages, promotes plaque stabilization and regression, and reduces inflammation.

Mg (II) has effects that parallel those of statins. For example, the enzyme that deactivates HMG-CoA reductase requires Mg (II), making Mg (II) a reductase controller rather than inhibitor. Mg (II) is also necessary for the activity of lecithin cholesterol acyl transferase (LCAT), which lowers LDL cholesterol and triglyceride levels and raises HDL cholesterol levels. Desaturase is another Mg (II)-dependent enzyme involved in lipid metabolism which statins do not directly affect. Desaturase catalyzes the first step in conversion of essential fatty acids (omega-3 linoleic acid and omega-6 linolenic acid) into prostaglandins, important in cardiovascular and overall health. Mg (II) at optimal cellular concentration is well accepted as a natural calcium channel blocker. More recent work shows that Mg (II) also acts as a statin. (Rosanoff A, Seelig M S. *J Am Coll Nutr* 23:501S-505S, 2004).

In some embodiments, between about 20 mg to 400 mg of magnesium is included in a composition of the invention, preferably, between about 38.5 mg to 384.6 mg (20% to 100% DV), on a weight basis.

Calcium

Calcium ($Ca^{+2}$) and lipids bind to one another in the gut, each interfering with the other's absorption. Ca (II) also causes malabsorption of bile acids, which is likely to contribute further to malabsorption of fat. High dietary Ca (II) intake also has stimulatory effect on lipolysis. Accordingly, Ca (II) supplementation could impact the plasma lipid concentrations. (Reid I R. *Drugs Aging* 21:7-17, 2004).

In some embodiments, between about 10 to 1200 mg (10% to 120% DV) of calcium is included in a composition of the invention, preferably between about 250 to 750 mg (25% to 75% DV), on a weight basis.

Chromium

Chromium ($Cr^{+2}$) lowers total and LDL cholesterol levels and raises HDL cholesterol levels in the blood, particularly in people with high cholesterol. Cr supplementation can improve glucose metabolism in glucose intolerant individuals and decrease the total/HDL cholesterol ratio regardless of the status of glucose tolerance. (Wallach S. *J Am Coll Nutr* 4:107-120, 1985; Broadhurst C L, Domenico P. *Diabetes Technol Ther* 8:677-687, 2006).

Chromium is generally utilized as a complex. There are various chromium complexes available that can be included in the compositions of the invention. These include, but are not limited to, chromium chloride, chromium picolinate, chromium chloride, chromium nicotinate, and high-chromium yeast.

Chromium picolinate is a widely used nutritional supplement for optimal insulin function. Chromium picolinate can lead to significant improvements in body composition resulting from fat loss, particularly for individuals who may not be as aggressive in making lifestyle changes such as reducing caloric intake or increasing their physical activity.

In some embodiments, between about 6 to 600 micrograms (5% to 500% DV) of chromium is included in a composition of the invention, preferably between about 30 to 300 micrograms (25% to 250% DV), on a weight basis.

Selenium

Selenium (Se) is a trace mineral that is essential to good health but required only in small amounts. Selenium is incorporated into proteins to make seleno-proteins, which are important antioxidant enzymes.

Selenium occurs in staple foods such as corn, wheat, and soybean as selenomethionine, the organic selenium analogue of the amino acid methionine. Selenomethionine can be incorporated into body proteins in place of methionine, and serves as a vehicle for selenium storage in organs and tissues. Selenium supplements may also contain sodium selenite and sodium selenate, two inorganic forms of selenium. Selenomethionine is generally considered to be the best absorbed and utilized form of selenium. Selenium is also available in 'high selenium yeasts', which may contain as much as 1,000 to 2,000 micrograms of selenium per gram. Most of the selenium in these yeasts is in the form of selenomethionine. (Schrauzer G N. *J Am College of Nutr* 20:1-4, 2001).

Selenium is one of a group of antioxidants that may help limit the oxidation of LDL cholesterol and thereby help to prevent coronary artery disease. Currently there is insufficient evidence available to recommend selenium supplements for the prevention of coronary heart disease. (Neve J. *J Cardiovasc Risk* 3:42-47, 1996).

In some embodiments, between about 6.9 to 345 micrograms (10% to 500% DV) of selenium is included in a MP-T3 composition of the invention, preferably between about 34.5 to 138 micrograms (50% to 200% DV), on a weight basis.

Optional Additives

In some embodiments, MP-T3 formulations of the present invention may further include optionally one or more additives. Optional additives of the present composition include, without limitation, acceptable carrier, such as oils, or other suspending agents; phospholipids, starches, sugars, fats, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

Suitable carriers include but are not limited to, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. The DHA or EPA can be in the form of an ester, such as a methyl ester. Alternatively or in combination with one of the above identified carriers, beeswax can be used as a suitable carrier, as well as suspending agents such as silica (silicon dioxide).

In embodiments where DHA or EPA or mixtures thereof (as an acid, an ester or mixtures thereof) are included in a MP-T3 formulation of the invention, between about 10 milligrams to 200 milligrams of EPA, preferably, between about 25 milligrams to 150 milligrams, and more preferably between about 50 milligrams to 100 milligrams are included on a weight basis.

Suitable ranges for DHA are from about 5 milligrams to 250 milligrams, in particular between about 15 milligrams and about 150 milligrams, and more particularly between about 25 milligrams and about 100 milligrams on a weight basis.

In some preferred embodiments, the MP-T3 composition is delivered as a first composition in a tablet or capsule and a second composition is administered which includes compounds which are a source of dietary fiber which is beneficial to reduce serum cholesterol. In preferred embodiments, the dietary fiber includes maltodextrin, glucomannan, guar gum, locust bean gum, prickly pear cactus and combinations thereof. Other components that may be included are hydrocolloid compound(s) such as edible celluloses, arabinogalactans, β-glucans, arabinoxylans, glucuronoxylans, xyloglucans, galactomannans, methyl cellulose, hydroxypropylmethyl cellulose (HPMC), inulin, oligofructans, xanthan gum, guar gum, locust bean gum, gum acacia, gum karaya, gum tragacanth, resistant starches, chemically synthesized polydextrose, lactulose, cellulose derivatives, methyl cellulose, hydroxypropylmethylcellulose, egg lecithin, soybean lecithin, vegilecithin, vitellin, short chain fructooligosaccharides (FOS), transgalactooligosaccharides (TOS), levan, oligofructose, xylooligosaccharides (XOS), curdlan, chitin, chitosan, collagen and chondroitin.

Preferably, the second composition that includes the dietary fiber is administered as a liquid. Preferably, the second composition is provided in a concentrated form, such as a concentrated liquid or gel or a dry powder to be dissolved in liquid before administration. Preferably the liquid is water, but any liquid may be used such as juice or milk. In a preferred embodiment, the both the first composition and the second composition are administered to the patient daily to maximize benefits.

The first composition and the second composition may be packaged together in a kit containing multiple doses of both the first and second compositions. Doses may be partitioned such that administration is one or multiple daily doses, preferably 1-4 times daily. It is not necessary that the first composition and the second composition be administered together for maximum benefit. Furthermore, the first composition may be administered more or less frequently than the second composition. However, in preferred embodiments, both the first composition and the second composition are administered daily.

EXAMPLES

The MP-T3 compositions of the invention will generally be used in an amount effective to achieve the intended result, for example in an amount effective to treat or prevent the particular affliction being treated. The MP-T3 can be administered to achieve therapeutic or prophylactic benefits. The therapeutic benefit is meant eradication or amelioration of the underlying disorder being treated and/or eradication or amelioration of one or more of the symptoms associated with the underlying disorder such that the individual reports an improvement in feeling or condition, notwithstanding that the individual may still be afflicted with the underlying affliction.

For example, administration of a MP-T3 formulation to an individual suffering from increased levels of cholesterol provides therapeutic benefit not only when the underlying condition is eradicated or ameliorated, but also when the individual reports a decrease in cholesterol from the blood serum. Therapeutic benefit also includes halting or slowing the progression of the disease, regardless of whether improvement is realized.

For prophylactic administration, the MP-T3 compositions of the invention can be administered to an individual at risk of developing one of the previously described health conditions. For example, if it is unknown whether an individual is likely to develop hypercholesterolemia, the MP-T3 can be taken to avoid or ameliorate such condition. Alternatively, prophylactic administration can be applied to avoid the onset of symptoms in an individual diagnosed with the underlying disorder.

Methods for preparing therapeutic and prophylactic formulations of MP-T3 are well known in the art and described in more detail in various sources, including, for example, Remington's Pharmaceutical Science (15th ed., Mack Publishing, Easton, Pa., 1980) (incorporated by reference in its entirety for all purposes).

For oral administration, MP-T3 can be given in solid dosage forms, such as capsules, tablets and powders, or in liquid dosage forms, such as elixirs, syrups, and suspensions. [0106] In some embodiments, the MP-T3 formulation may be administered in a bar, such as a chocolate bar. The bar may be either molded to form "rectangular bar" shapes that are then allowed to solidify to form the final product. The following examples are intended to be illustrative only and should not be considered limiting.

Example 1

MP-T3 Soft-Gel Formulations

Exemplary soft gel, soft gelatin or soft vegetable capsules can be prepared, without limitation, by dispersion of MP-T3 blend in an appropriate vehicle to form a high viscosity mixture, by using conventional methods well known in the art. Soft elastic gelatin capsules have a soft, globular gelatin shell, somewhat thicker than that of hard gelatin capsules. In such soft gel formats, gelatin is plasticized by the addition of plasticizing agent, e.g., glycerin, sorbitol, or a similar polyol. The hardness of the capsule shell can be altered with the appropriate type of gelatin and amounts of plasticizer and water. Soft gelatin shells may contain a preservative, such as methyl- and propylparabens and sorbic acid, to prevent any fungal growth. MP-T3 blend may be dissolved or suspended in a liquid vehicle or carrier, such as vegetable or mineral oils, glycols such as polyethylene glycol and propylene glycol, triglycerides, surfactants such as polysorbates, or a combination thereof.

TABLE 1

| INGREDIENT | LF-based | OTF-based* | ANGex-based** |
|---|---|---|---|
| Metallo-Protein Complex | 120 mg | 75 mg | 100 mg |
| T3 (from palm) oil form | 100 mg | 50 mg | 100 mg |
| Oryzanol | 50 mg | 50 mg | 50 mg |
| Flaxseed oil | 75 mg | 100 mg | 75 mg |
| Pycnogenol | 150 mg | 100 mg | 150 mg |
| Nicotinic acid (250% DV) | 50 mg | 50 mg | 50 mg |
| Pantethine (250% DV) | 25 mg | 25 mg | 25 mg |
| Chromium (polynicotinate) (100% DV) | 120 mcg | 120 mcg | 120 mcg |
| Magnesium (5% DV) | 20 mg | 20 mg | 20 mg |

*OTF can be substituted with metallo-thionein (MT)
**ANGex - preferably lactoferrin with milk angiogenin.

In preferred embodiments, the weight of the capsule may range between about 100 to 2500 milligrams; preferably, weigh between about 500 and 2000 milligrams; and more preferably, weigh between about 750 and 1500 milligrams.

Example-2

MP-T3 Two-Piece HSC (Hard Shell Capsule) Formulations

Exemplary 2-piece HSC capsules can be prepared, without limitation, in an appropriate carrier system to encapsulate MP-T3 mixture, by using conventional methods well known in the art.

TABLE 2

| INGREDIENT | LF-based | OTF-based* | ANGex-based** |
|---|---|---|---|
| Metallo-protein complex | 120 mg | 75 mg | 100 mg |
| T3 (from palm) powder form | 75 mg | 100 mg | 50 mg |
| Astaxanthin | 75 mg | 75 mg | 50 mg |
| Pycnogenol | 100 mg | 100 mg | 150 mg |
| Nicotinic acid (200% DV) | 40 mg | 40 mg | 40 mg |
| Pantethine (200% DV) | 20 mg | 20 mg | 20 mg |
| Selenium (Selenomethionine) | 69 mcg | 69 mcg | 69 mcg |
| Magnesium (as oxide) (5% DV) | 20 mg | 20 mg | 20 mg |

*OTF can be substituted with metallo-thionein (MT)
**ANGex - preferably lactoferrin with milk angiogenin.

A composition of MP-T3 is formulated with the ingredients listed above and the mixture was encapsulated in a two-piece capsule according to methods commonly practiced in the art of manufacturing of dietary supplements. The capsular shell materials suitable for the above encapsulation include but is not limited to gelatin-based, cellulose-based and vegetable-based compounds.

Example-3

MP-T3 Tablet Formulations

Exemplary tablets with MP-T3 formulations of the present invention can be prepared, without limitation, with appropriate excipients, by using conventional methods well known in the art.

TABLE 3

| INGREDIENT | LF-based | OTF-based* | ANGex-based** |
|---|---|---|---|
| Metallo-protein complex | 120 mg | 75 mg | 100 mg |
| T3 (from palm) powder form | 100 mg | 75 mg | 100 mg |
| Grape seed extract (95%) | 150 mg | 150 mg | 200 mg |
| Phytosterol 90% (Beta-sitosterol) | 500 mg | 500 mg | 300 mg |
| Nicotinic acid | 50 mg | 50 mg | 25 mg |
| Pantethine | 20 mg | 25 mg | 20 mg |
| Biotin | 150 mcg | 150 mcg | 300 mcg |
| Chromium (as nicotinate) | 48 mcg | 48 mcg | 48 mcg |
| Selenium (Selenomethionine) | 105 mcg | 105 mcg | 105 mcg |
| Magnesium (as oxide) | 60 mg | 30 mg | 20 mg |

*OTF can be substituted with metallo-thionein (MT)
**ANGex - preferably lactoferrin with milk angiogenin.

Tablets with MP-T3 formulations can be prepared with pharmaceutically acceptable excipients including fructose-DC, magnesium stearate, stearic acid, CanTab (tableting dextrose, Penford Food Ingredients, Englewood, Colo.), natural flavor and color (if necessary) were blended with the ingredients from Table 3. Each of the above ingredients was placed, in powdered form, into a commercial blender, mixed and, if necessary, passed through a mesh screen to remove aggregates. After 20 minutes of thorough mixing, the composition is cold pressed in a tablet press set at a appropriate pressure and manufacturing methods commonly practiced in the art of manufacturing dietary supplements.

Example-4

Exemplary MP-T3 Drink Mix Formulations

In the following example, a formulation designed to facilitate cholesterol management is presented. The MP-T3 compositions of the present invention may be provided in a variety of formats, including but not limited to, liquid form, or powder form. Powders are preferable and are prepared to be suitable for mixing with water or other liquids. The MP-T3 compositions in powder or granular form may be provided in accordance with customary processing techniques, for example as spray dried powders, or the like.

TABLE 4

| INGREDIENT | LF-based | ANGex-based* |
|---|---|---|
| Metallo-Protein Complex | 30 mg | 30 mg |
| T3 (from palm) powder form | 25 mg | 25 mg |
| Glutathione (reduced) | 30 mg | 30 mg |
| Nattokinase | 20 mg | 20 mg |
| Coenzyme-Q10 | 30 mg | 30 mg |
| Coenzyme R (as Biotin) 25% DV | 75 mcg | 75 mcg |
| Vitamin B1 (as Thiamin) 100% DV | 1.5 mg | 1.5 mg |
| Vitamin B2 (as Riboflavin) 100% DV | 1.7 mg | 1.7 mg |
| Vitamin B3 (as Nicotinic acid) 250% DV | 50.0 mg | 50.0 mg |
| Vitamin B5 (Pantothenic acid) 250% DV | 25.0 mg | 25.0 mg |
| Vitamin B6 (as Pyridoxine HCl) 100% DV | 2.0 mg | 2.0 mg |
| Vitamin B9 (as Folic acid) 100% DV | 400 mcg | 400 mcg |
| Vitamin B12 (as Cyanocobalamin) 250% DV | 15 mcg | 15 mcg |
| L-carnitine | 500 mg | 500 mg |
| Limonin glucoside | 200 mg | 200 mg |
| Magnesium (31% as citrate) | 30 mg | 30 mg |
| Chromium (polynicotinate) | 120 mcg | 120 mcg |
| Sodium bicarbonate | 200 mg | 200 mg |
| Citric acid | 200 mg | 200 mg |
| Maltodextrin | 1000 mg | 1000 mg |
| Glucomannan | 1500 mg | 1500 mg |

*ANGex - preferably lactoferrin with milk angiogenin.

As shown above in Table-4, the MP-T3 is formulated with the addition of nicotinic acid, pantothenic acid, L-carnitine, limonine glucoside, glucomannan to suit the cholesterol management regimen.

In one alternative embodiment of the present invention, an appropriate serving of a drink may also contain CoQ-10, B-complex vitamins and/or minerals such that it provides appropriate nutrition or even increase energy levels in the body.

The MP-T3 formulation suitable for beverage use in the present invention includes, but is not limited to, any flavored drink comprising sugar, malic acid, aspartame, sodium citrate, natural and artificial flavors/colors.

Example 5

Exemplary MP-T3 "Two-Component" Cholesterol Management Formulation for a Preventive and Therapeutic Management of Hypercholesterolemia, Hyperlipidemia and Hyperlipoproteinemia The exemplary MP-T3 composition uses a synergistic 'Two-Component' delivery system. This novel system includes MP-T3 formulated in a tablet form (Component-1), orally administered in combination with a beverage mix (Component-2) comprising hygroscopic fiber that could interfere with lipid absorption in the intestinal tract. Exemplary tablets and beverage mix of the 2-Component formulation of the present invention can be prepared, without limitation, with appropriate excipients, by using conventional methods well known in the art.

TABLE 5A

| (COMPONENT-1) | | |
|---|---|---|
| INGREDIENT | Per Serving | % DV |
| Metallo-protein complex (ANGex-based)* | 105 mg | † |
| T3 (from plam) beadlet form | 200 mg | † |
| Artichoke (dry) extract | 250 mg | † |
| Vitamin-B3 (as niacinamide) | 30 mg | 150% |
| Vitamin-B5 (as calcium D-pantothenate) | 20 mg | 200% |
| Biotin | 200 mcg | 66% |
| Selenium (as L-selenomethionine) | 60 mcg | 86% |
| Chromium (as nicotinate) | 48 mcg | 40% |
| Magnesium (as stearate or oxide) | 40 mg | 10% |
| Calcium (as carbonate) | 72 mg | 8% |

*ANGex - preferably lactoferrin with milk angiogenin (ribonuclease types 2 & 4).

Exemplary COMPONENT-1 of the above MP-T3 formulation of the present invention can be prepared in a tablet form, without limitation, with appropriate excipients, and natural colorants such as chlorophyllin, by using conventional methods well known in the art.

TABLE 5B

| (COMPONENT-2) | | |
|---|---|---|
| Active Ingredient | Per Serving | % DV |
| Grape-seed extract | 250 mg | † |
| Bromelain (pineapple extract) | 25 mg | † |
| Sodium bicarbonate | 200 mg | † |
| Citric acid | 200 mg | † |
| Maltodextrin | 1000 mg | † |
| Glucomannan (konjac root) | 1200 mg | † |
| Citrus bioflavonoid | 200 mg | † |

As shown above in Table-5B, the COMPONENT-2 is a beverage mix in powder form suitable for mixing with water or other liquids. The formulation consists of fiber that includes glucomannan (from *konjac* root) and maltodextrin to synergistically enhance the MP-T3 activity in reducing the serum cholesterol. The beverage mix also includes, but is not limited to, sweeteners comprising fructose, stevia leaf extract, natural sweet enhancer; natural flavors, including but not limited to apple powder, and natural apple flavor; malic acid, magnesium aspartate; and emulsifiers including but not limited to guar gum, cellulose gum, and inulin.

In preferred embodiments, COMPONENT-1 and COMPONENT-2 are administered 2-3 times per day. However, more frequent or less frequent administration may be indicated depending on the needs, state of health or disposition of the individual in need of preventive and/or therapeutic management of hypercholesterolemia, hyperlipidemia and/or hyperlipoproteinemia. Furthermore, while the two components are intended for administration together, it is not necessary to administer both components at the same time or in the same number of servings per day. For example, it may be convenient to administer COMPONENT-1 three times daily with meals and COMPONENT-2 in the morning and evening. Although maximal benefit is achieved by administration of both COMPONENT-1 and COMPONENT-2, benefit may also be obtained by administration of COMPONENT-1 or COMPONENT-2 separately.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A composition comprising tocotrienol (T3), wherein the T3 is from a natural source and at least one metalloprotein, wherein the at least one metallo-protein is a combination of lactoferrin and angiogenin.

2. The composition of claim 1, wherein the T3 is a mixture of tocotrienols that comprise alpha-T3, beta-T3, gamma-T3 and delta-T3 forms or isomers.

3. The composition of claim 1, wherein the natural source is oil or an oleoresin powder selected from the group consisting of wheat germ, barley, saw palmetto, palm and rice bran.

4. The composition of claim 3, wherein the natural source is palm oil, palm oleoresin powder, rice bran oil or rice bran oleoresin powder.

5. The composition of claim 1, further comprising at least one angiogenic factor selected from the group consisting of vascular endothelial growth factors (VEGF), fibroblast growth factors (FGF), and transforming growth factors (TGF).

6. The composition of claim 1, further comprising at least one vitamin selected from the group consisting of Vitamin A, Vitamin C, Vitamin E (alpha, beta, gamma and delta forms of tocopherols), Vitamin D, and Vitamin K and B vitamins including thiamine (Vitamin $B_1$), Riboflavin (Vitamin $B_2$), Niacin/Vitamin $B_3$ (defined as nicotinic acid, nicotinamide, NAD, NADH and NADP), Pantothenic acid (Vitamin $B_5$), Pyridoxine and Pyridoxamine (Vitamin $B_6$), Biotin (Vitamin $B_7$), Folic Acid (Vitamin $B_9$) and Cobalamin (Vitamin $B_{12}$).

7. The composition of claim 1, further comprising at least one mineral supplement selected from the group consisting of calcium, magnesium, chromium, and selenium and pharmaceutically acceptable salts thereof.

8. A food or drink comprising the composition of claim 1.

9. A method of lowering levels of LDL cholesterol comprising administering a composition of claim 1 comprising tocotrienol (T3), wherein the T3 is from a natural source, and at least one metalloprotein, wherein the at least one metalloprotein is a combination of lactoferrin and angiogenin, to an individual in need thereof at a dosage sufficient to lower LDL cholesterol.

10. The method of claim 9, wherein the administered dosage comprises 10-1000 mg of T3 per day.

11. The method of claim 10, wherein the administered dosage comprises 25-250 mg of T3 per day.

12. A method of treating a disease condition comprising administering a composition comprising a mixture of tocotrienol (T3) and at least one metallo-protein (MP) to an individual in need thereof, wherein the MP-T3 mixture is from a natural source, and wherein the at least one metallo-protein is a combination of lactoferrin and angiogenin, and wherein the disease condition is selected from the group consisting of diabetes, neurodegenerative diseases, cardiovascular diseases, atherosclerosis and hypercholesterolemia.

13. A kit comprising:
a first composition comprising the composition of claim 1; and
a second composition comprising a soluble fiber.

14. The kit of claim 13, wherein the T3 is a mixture of tocotrienol isomers alpha-T3, beta-T3, gamma-T3 and delta-T3.

15. The kit of claim 13, wherein the natural source is palm oil in beadlet form.

16. The kit of claim 13, wherein the first composition further comprises Vitamin $B_3$ as nicotinamide, calcium-D-pantothenate (Vitamin $B_5$), and Biotin (Vitamin $B_7$).

17. The kit of claim 13, wherein the first component is in tablet or capsule form and the second component is administered as a liquid.

18. The kit of claim 13, wherein the second component is a dry powder or concentrate that is mixed with a liquid before administration.

19. The kit of claim 13, wherein the soluble fiber is selected from the group consisting of glucomannan, maltodextrin, and combinations thereof.

20. The kit of claim 13, wherein the first composition further comprises calcium (as carbonate), magnesium (as stearate or oxide), chromium (as nicotinate), and selenium (as 1-selenomethionine).

21. A method of treating hypercholesterolemia, hyperlipidemia or hyperlipoproteinemia comprising administering to an individual in need thereof in any order:
a first composition comprising T3 and a metallo-protein, wherein the T3 is from a natural source and wherein the metallo-protein is a combination of lactoferrin and angiogenin; and
a second composition comprising a soluble fiber wherein said first and second compositions are administered at a dosage sufficient to treat hypercholesterolemia, hyperlipidemia or hyperlipoproteinemia.

22. The method of claim 21, wherein the first composition is in tablet or capsule form and the second component is administered as a liquid.

23. The method of claim 21, wherein the administered dosage comprises 10-1000 mg of T3 per day.

24. The method of claim 23, wherein the administered dosage comprises 25-250 mg of T3 per day.

* * * * *